US005342315A

United States Patent [19]

Rowe et al.

[11] Patent Number: 5,342,315

[45] Date of Patent: Aug. 30, 1994

[54] TROCAR SEAL/PROTECTOR ASSEMBLIES

[75] Inventors: C. Daniel Rowe, Batavia; Leslie R. Ashmore, Maineville; Chad C. Carroll, East Canton; Richard F. Schwemberger, Cincinnati; Norman F. Schuler, West Chester, all of Ohio; John M. Collins, Ipswich, Mass.

[73] Assignee: Ethicon, Inc., Cincinnati, Ohio

[21] Appl. No.: 46,089

[22] Filed: Apr. 12, 1993

[51] Int. Cl.[5] ..................... A61M 5/18

[52] U.S. Cl. ..................... 604/167

[58] Field of Search ............... 606/185; 604/164, 166, 604/167, 264

[56] References Cited

U.S. PATENT DOCUMENTS

| | | | |
|---|---|---|---|
| 3,313,299 | 4/1967 | Spademan | 128/214.4 |
| 3,585,996 | 6/1971 | Reynolds et al. | 128/214.4 |
| 4,096,860 | 6/1978 | McLaughlin | 128/214.4 |
| 4,177,814 | 12/1979 | Knepshield et al. | 128/348 |
| 4,240,411 | 12/1980 | Hosono . | |
| 4,261,357 | 4/1981 | Kontos | 128/214.4 |
| 4,535,773 | 8/1985 | Yoon | 604/51 |
| 4,540,411 | 9/1985 | Bodicky | 604/169 |
| 4,581,019 | 4/1986 | Curelaru et al. | 604/164 |
| 4,629,450 | 12/1986 | Suzuki et al. | 604/164 |
| 4,670,008 | 6/1987 | Von Albertini | 604/165 |
| 4,723,550 | 2/1988 | Bales et al. | 128/344 |
| 4,729,914 | 3/1988 | Kliment et al. | 428/36 |
| 4,772,264 | 9/1988 | Cragg | 604/158 |
| 4,862,891 | 9/1989 | Smith | 128/343 |
| 4,935,008 | 6/1990 | Lewis, Jr. | 604/52 |
| 4,950,257 | 8/1990 | Hibbs et al. | 604/265 |
| 4,954,130 | 9/1990 | Edwards | 604/169 |
| 4,978,334 | 12/1990 | Toye et al. | 604/51 |
| 4,981,482 | 1/1991 | Ichikawa | 606/108 |
| 4,994,027 | 2/1991 | Farrell | 604/53 |
| 5,000,745 | 3/1991 | Guest et al. | 604/167 |
| 5,009,643 | 4/1991 | Reich et al. | 604/165 |
| 5,030,206 | 7/1991 | Lander | 604/164 |
| 5,041,097 | 8/1991 | Johnson | 604/167 |
| 5,092,846 | 3/1992 | Nishijima et al. | 604/165 |
| 5,112,308 | 5/1992 | Olsen et al. | 604/164 |
| 5,180,373 | 1/1993 | Green et al. | 604/167 |
| 5,197,955 | 3/1993 | Stephens et al. | 604/167 |
| 5,209,736 | 5/1993 | Stephens et al. | 604/164 |
| 5,209,737 | 5/1993 | Ritchart et al. | 604/167 |
| 5,211,370 | 5/1993 | Powers | 251/4 |

FOREIGN PATENT DOCUMENTS

| | | |
|---|---|---|
| 0267584 | 11/1987 | European Pat. Off. . |
| 0316096 | 10/1988 | European Pat. Off. . |
| 0426407 | 10/1990 | European Pat. Off. . |
| 0510851 | 4/1992 | European Pat. Off. . |
| WO 93/04717 | 3/1993 | PCT Int'l Appl. . |

*Primary Examiner*—Jerome L. Kruter

*Attorney, Agent, or Firm*—Dressler, Goldsmith, Shore & Milnamow

[57] ABSTRACT

Trocar assembly embodiments are disclosed that include a trocar tube and a housing defining a chamber adjoining a proximal end portion of the trocar tube. An elastomeric seal member is positioned within the chamber for sealing the chamber as an elongate instrument passes through an opening formed in the seal member. A seal/protector assembly is positioned in the chamber proximally of the seal member in facing relationship to the seal member. The protector assembly includes at least two axially aligned protector members, each of which has an annular collar portion and at least one leaf portion formed integrally with the collar portion so as to form a living hinge portion. The leaf portions define an opening therethrough in axial alignment with the opening in the seal member. Insertion of an elongate instrument into contact with the leaf portions causes them to pivot distally increasing the size of the opening formed thereby permitting the instrument to pass therethrough and through the opening in the seal member without causing damage to the seal member.

48 Claims, 23 Drawing Sheets

772 768 760 764 766 750 762 734 768 790 753 744 760 748 780

32
14
24
16
10
20
22
12
18

32
82
64
62
60
26
42
80
10
46
50
58
34
54
44
48
24
53
56
52
38
40
36
16
22

5
78
72
64
70
66
76
4
4
74
68
76
78
5

78
66
72
70
76
74

78
66
78
78
68
70
76
74

78
64
72
66
68
78
62
66
76
76
72
72
70
68

9
178
164
8
168
8
174
166
172
9

178
166
174
168

178
166
172
168

178
164
166
172
168
160
178
163
172
166
168
168
178
162
166
172
168

278
264
268
266
13
13
274
272
268

266
278
262
272
268
274
268

278
266
272
268
274

268
274

278
264
266
274
268
260
268
278
262
272
266
268
274

378
368
364
360
362
334
354
353
335
337
369
348

364
372
366
378
374
368

366
378
372
374
362
368

34
50
35
44
48
46
54
53

26
578
562
25
25
566
574
568
26

566
578
572
568

566

578
568
568
574

434
450
28
28
454
448
446
453
444

450
434
454
446
444
448
453

772
768
760
766
764
750
762
734
753
768
790
744
760
748
780

34
750
754
744
734
748
33
33
751
760
753
34

750
751
734
746
754
744
753
760
762
748
764

750
734
751
746
754
760
764
762
753
744
748

868
860
864
862
880
884
852
848
874
882
334

42

864
868
872
874
42

866
864
872
868
880
882
874

874
880
882
868
864

854
853
834
851
844
852
850
45
45
848

862
874
48
48
892
868
866

846
851
850
854
853
844
852
848
834

866
872
892
862
868
884
874

834
853
852
848
851
844

862
892
874
884
868

978
968
964
962
984
952
948
974
982
934

52

968
964
978
974
972
52

966
964
972
968
982
974

978
982
964
968

954
953
950
934
952
55
55
948
944

978
962
974
58
58
968
966

950

946
954
953
944
952
948
934

978
972
966
962
968
984
974

934
952
948
944
953

962
984
974
968

1080
1062
1034
1044
1064
1083
1050
1042
1046
1043
1045
1049
1082
1048
1051
1047
1057
1059
1026
1071
1055
1053
1061
1033
1024
1028
1031
1010
1038
1036
1040
1016
1012

1083
1064
1085
1034
1080
1062
1087
1050
1043
1046
1042
1082
1088
1045
1044
1086
1049
1047
1051
1053

1050
1085
1087
1042
1064
1062
1074
1060
1034
1043
1088
1048
1086
1049
1047
1045
1051
1053

1085
1087
1050
1064
1062
1074
1060
1034
1042
1043
1048
1088
1086
1049
1047
1045
1051
1053

1087
1085
1060
1042
1050
1064
1062
1074
1043
1048
1086
1034
1088
1049
1047
1045
1051
1053

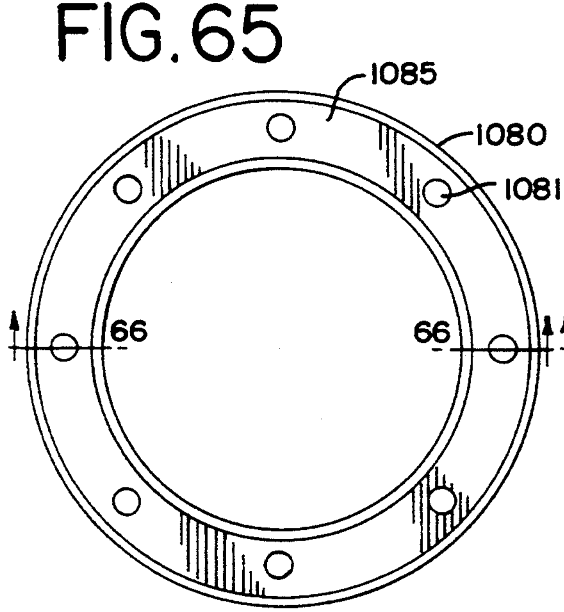
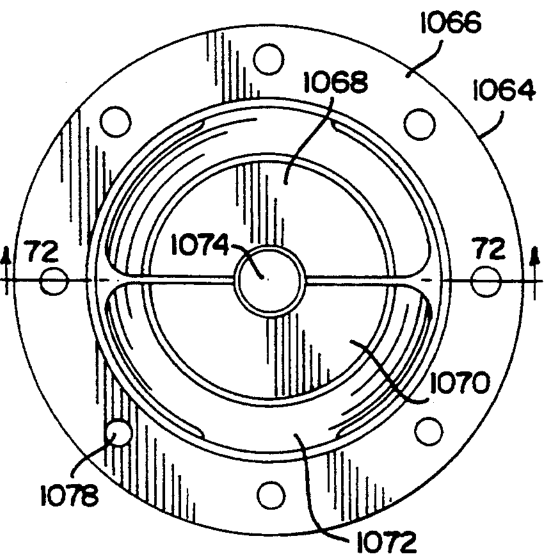
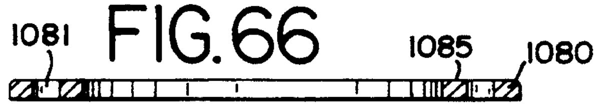
FIG. 70
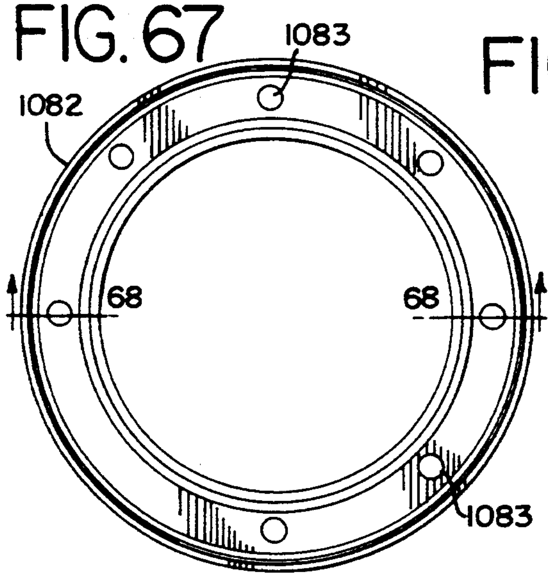
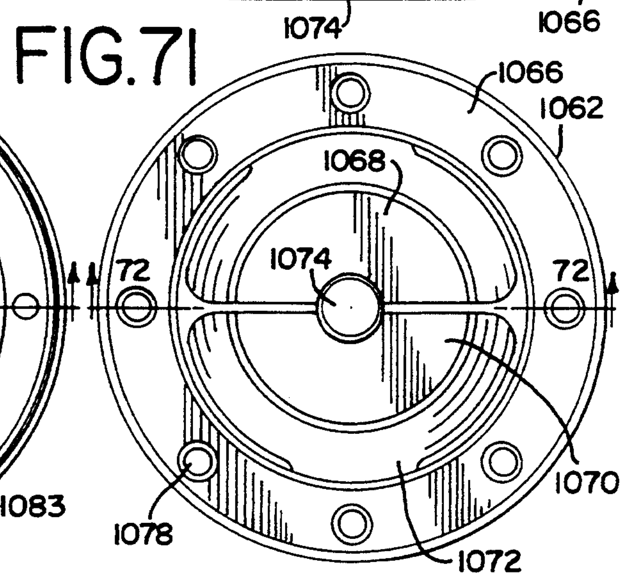
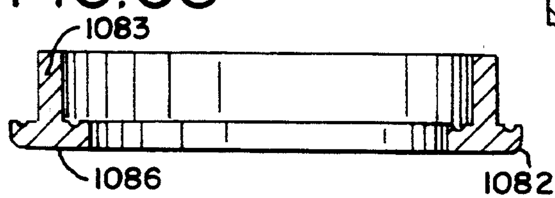
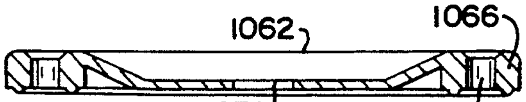

1243
81
1242
1245
1260
1244
1262
1234
1264
1285
1280
1246
1228
1248
1245
1233
1271
1226
1261
1210
1224
1216
1238
1212
1240
1236
1249
1259
1247
1255
1253

1383
1350
1380
1390
1346
1343
1342
1360
1364
1362
1334
1345
1349
1382
1348
1324
1359
1371
1355
1353
1316

1383
1350
1360
1380
1348
1334
1343
1346
1390
1362
1342
1364
1382
1345
1349
1324
1359
1371
1355
1353
1316

TROCAR SEAL/PROTECTOR ASSEMBLIES

FIELD OF THE INVENTION

This invention generally relates to surgical instruments; and more particularly, the invention relates to surgical trocar assembly devices for providing communication into an anatomical cavity. The trocar assembly devices in accordance with the present invention include a seal/protector assembly that protects the seal member during the insertion of elongate surgical instruments therethrough.

BACKGROUND OF THE INVENTION

A trocar assembly is a surgical instrument that is used to gain access to a body cavity. A trocar assembly generally comprises two major components, a trocar tube and an obturator. The trocar tube having the obturator inserted therethrough is directed through the skin to access a body cavity through the tube in which laparoscopic or arthroscopic surgery and endoscopic procedures are to be performed. In order to penetrate the skin, the distal end of the trocar tube is placed against the skin which has been cut with a scalpel. The obturator has a sharp point or cutting edge at its distal end. By applying pressure against the proximal end of the obturator, the sharp point is forced through the skin until it enters the body cavity. The trocar tube is inserted through the perforation made by the obturator and the obturator is withdrawn, leaving the trocar tube as an accessway to the body cavity. Examples of trocar assembly devices are disclosed in U.S. Pat. Nos. 4,535,773 and 5,066,288.

The proximal end portion of the trocar tube is typically adjoined by a housing that defines a chamber having an open distal end portion that communicates with the interior lumen defined by the trocar tube. An obturator and other elongate surgical instruments or tools axially extend into and are withdrawn from the trocar tube through the proximal end portion of the chamber. it is the present practice to provide the chamber with an outer sealing means, such as a sealing grommet or gasket, through which the obturator or other instruments extend. The sealing means seals against the outer surface of the inserted instruments and thereby prevents fluids from leaving or entering the body cavity through the trocar tube. Examples of sealing means are disclosed in commonly assigned copending U.S. Pat. Ser. No. 07/779,040, filed on Oct. 18, 1991, and U.S. Pat. Ser. No. 08/046,587, filed Apr. 12, 1993, entitled Improved Seal Members For Surgical Trocars, filed concurrently herewith, the disclosures of which applications are incorporated herein by reference.

In developing trocar assembly devices for use in connection with surgical instruments having broad ranges of outer diameters (e.g., 2–5 mm or 5–11 mm), it is required that the outer seal member have an opening that is very small relative to the outer diameter of the instruments in the upper end of the size range. The insertion of large diameter instruments having sharp edges, such a surgical clip appliers and the like, cause tearing of the seal member. Accordingly, there is a need for a trocar assembly that includes means to protect the outer seal during the insertion of such surgical instruments. It is further desirable that such a protector means assist in the centering of instruments directed therethrough and assist in the dilation of the opening in the seal member as the instruments pass therethrough. It is also desirable that the protector means reduce frictional drag as an instrument is inserted through the outer seal.

The reference to the axial movement of the instrument through the seal member is intended to include insertion and withdrawal of the instrument as well as relative in and out movement of the instrument.

SUMMARY OF THE INVENTION

In accordance with the principles of the present invention, trocar assembly devices are provided that include a seal/protector assembly comprising a protector assembly positioned in the trocar housing proximally of the outer seal member for protecting the seal member as an elongate instrument is inserted or withdrawn therethrough.

The protector assembly includes at least two protector members positioned in axial alignment with one another in a facing relationship to the seal member. Each of the protector members includes an annular collar portion and at least one leaf portion formed integrally with the collar portion so as to form a living hinge portion about which the leaf portion is able to pivot distally and proximally. The leaf portions define an opening therethrough in axial alignment with an opening in the seal member so that insertion of an elongate member into contact with the leaf portions causes the leaf portions to pivot distally increasing the size of the opening in the protector members to permit the instrument to pass therethrough and then through the opening in the seal member without causing damage to the seal member. The contact between the instrument and the seal is minimized, which results in less frictional drag and better feel and control by the surgeon.

In accordance with a preferred embodiment of the invention, the protector assembly includes an inner protector member and an outer protector member. The inner and outer protector members each include a pair of opposed leaf portions that occupy a substantial portion of the area defined within the collar portion. The leaf portion of the inner protector member is oriented with respect to a leaf portion of the outer protector member so that they are not in axial alignment with one another. The leaf portions are generally concave and define an inner edge that is parallel and immediately adjacent the inner edge of the other leaf portion.

The collar portions may be formed with a plurality of spaced apart openings formed therein and the trocar housing includes mounting pins that extend through a corresponding opening to secure the protector members to the housing. The openings may be elongated in a radial direction to permit lateral movement of the protector members in the housing. An annular spacer ring may be positioned between the inner protector member and the seal member.

In accordance with an alternative preferred embodiment of the invention, the protector assembly includes an intermediate protector member positioned between an inner protector member and an outer protector member. Each of the protector members includes a single leaf portion that occupies about two-thirds of the area defined within the collar portion. The leaf portions associated with each of the protector members is oriented with respect to one another so as to close the area defined within the collar portions except for the opening in axial alignment with the opening in the seal member.

In accordance with another embodiment of the invention, the protector assembly includes an inner and outer protector member. Each of the protector members include four generally pie-shaped leaf portions that occupy a substantial portion of the area defined within the collar portion.

Other alternative embodiments of the invention include various means to interlock the protector members to the seal member to facilitate dilation of the opening in the seal member and to enhance protection of the seal member as an elongate member extends therethrough. Other embodiments of the invention provide projections or ribs extending from the surfaces of the seal member and/or the protector members to facilitate dilation of the opening in the seal member.

Additional embodiments of the invention include protector members that are mounted in a manner that permits them to float laterally and/or longitudinally within the trocar housing. Such embodiments may include an adaptor assembly containing a seal member and the protector members that is releasably attached to the proximal end of a trocar.

BRIEF DESCRIPTION OF THE DRAWINGS

A more complete appreciation of this invention, and many of the attendant advantages thereof will be readily apparent as the same becomes better understood by reference to the following detailed description, when considered in conjunction with the accompanying drawings, in which reference numerals having the same last two digits indicate the same or similar components, wherein:

FIG. 65 is a top plan view of the outer retainer ring of the seal/protector assembly shown in FIG. 60;

FIG. 66 is a cross-sectional view taken along line 66—66 in FIG. 65;

FIG. 67 is a top plan view of the inner retainer ring of the seal/protector assembly shown in FIG. 60;

FIG. 68 is a cross-sectional view taken along line 68—68 in FIG. 67;

FIG. 69 is a top plan view of the outer protector member of the seal/protector assembly shown in FIG. 60;

FIG. 70 is a cross-sectional view taken along line 70—70 in FIG. 69;

FIG. 71 is a top plan view of the inner protector member of the seal/protector assembly shown in FIG. 60;

FIG. 72 is a cross-sectional view taken along line 72—72 in FIG. 71;

DETAILED DESCRIPTION OF PREFERRED EMBODIMENTS

Figure 1:
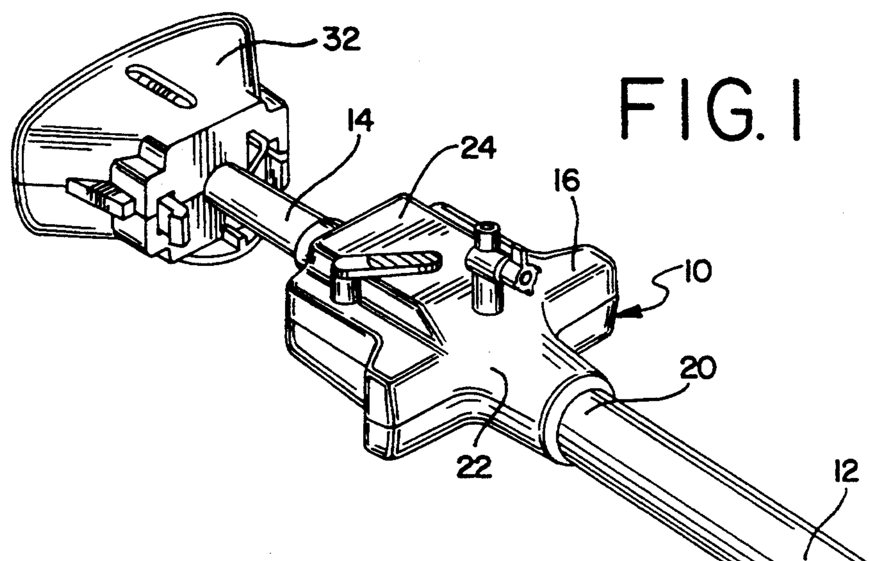
FIG. 1 is a perspective view of a trocar assembly device of the type that includes a seal/protector assembly constructed in accordance with the invention, with an obturator partially extended into the trocar tube.

Referring to FIGS. 1–6, there is shown a preferred embodiment of a trocar assembly device 10 that includes a seal/protector assembly 60 constructed in accordance with the invention. The specific construction of the trocar assembly device 10 does not form a part of the invention.

Trocar assembly device 10 includes a trocar tube 12, an obturator 14, and a housing or handle 16. Trocar tube 12 defines an interior lumen having an open distal end portion 18 and an open proximal end portion 20. Proximal end portion 20 extends into and is mounted in a distal end portion 22 of handle 16. Handle 16 has an open proximal end portion 24 that defines an opening 26. Opening 26 is provided with a seal/protector assembly 60 that includes an outer seal member 34.

Obturator 14 is slidably and removably extendable within trocar tube 12 and is inserted into handle 16 and trocar tube 12 through seal/protector assembly 60 and opening 26. An obturator handle 32 is provided at the proximal end of the obturator and a sharpened point or blade (not shown) is formed at the distal end thereof. As is well known in the art, seal/protector assembly 60 cooperates with obturator 14, or a surgical instrument extending through trocar tube 12, to sealingly engage the outer surface thereof and thereby preclude the passage of fluids through handle 16.

A flap valve assembly 36 is suitably supported in end portion 24. Flap valve assembly 36 defines a passageway 38 having a hinged flap valve 40 at the distal end thereof and an elastomeric seal member 34 at the proximal end thereof. A rigid guide/retainer 42 is preferably secured within end portion 24 to guide an obturator or implement through seal member 34 into passageway 38 and to retain the seal member.

Elastomeric seal member 34 is generally of the type disclosed in U.S. patent application Ser. No. 07/779,040, filed on Oct. 18, 1991, and U.S. patent application Ser. No. 08/046,587, entitled Improved Seal Members For Surgical Trocars, assigned to the same assignee as the present invention and filed concurrently herewith, the disclosure of which patent applications are incorporated herein by reference. Seal member 34 includes a generally planar inner section 44 and an outer section 46. An opening 48 is formed through inner section 44 and is dimensioned to permit an obturator or instrument to pass therethrough in sealing engagement therewith. A corrugated portion 50 is formed in outer section 46 in surrounding relationship with opening 48. A plurality of spaced apart projections or ribs 52 may be provided to extend outwardly from the surfaces of the planar inner section 44 of the seal member and radially with respect to opening 48. Projections 52 may be integrally formed in inner section 44. Outer section 46 is formed with a proximally extending annular flange portion 53 having a groove or recess 54 formed therein. Flange portion 53 is received in an annular recess 56 formed in flap valve assembly 36. Guide/retainer member 42 includes a distally extending edge portion 58 that is received in recess 54 to retain seal member 34 in sealing engagement with flap valve assembly 36.

In accordance with the invention, seal/protector assembly 60 includes protector members that are located in the chamber of housing or handle 16 proximally of and in facing relationship to the seal member 34 for protecting the seal member as an elongate instrument is inserted therethrough. Referring to FIGS. 3–6, seal/protector assembly 60 includes an inner protector member 62 and an outer protector member 64 which, when assembled, are positioned in axial alignment with one another.

Protector members 62 and 64 are of substantially identical construction and include an annular collar portion 66 and a pair of opposed leaf portions 68 and 70 formed integrally with collar portion 66 so as to form a living hinge portion 72 about which the leaf portions are able to pivot distally and proximally. The leaf portions occupy a substantial portion of the area defined within the collar portion.

The leaf portions 68 and 70 define an opening 74 formed therethrough in axial alignment with the opening 48 formed in seal member 34. An inserted elongate member contacts the leaf portions and causes them to move distally with the seal member increasing the size of the opening 74 in the protector members to permit the instrument to pass therethrough and then through the opening 48 in the seal member, without causing damage to the seal member. As the leaf portions move distally, they contact the seal member causing the opening 48 to dilate and increase in diameter. In so doing, the trocar assembly is able to accommodate instruments of different ranges of diameters. For example, it is anticipated that the range of instrument diameters would be from about 2 to about 5 mm or from about 5 to about 11 mm. The protector members further act to center the instrument by virtue of the forces needed to extend the instrument through the seal member. The seal/protector assembly seals against instruments that vary in diameter while permitting them to function in off-centered orientations.

Figure 6:
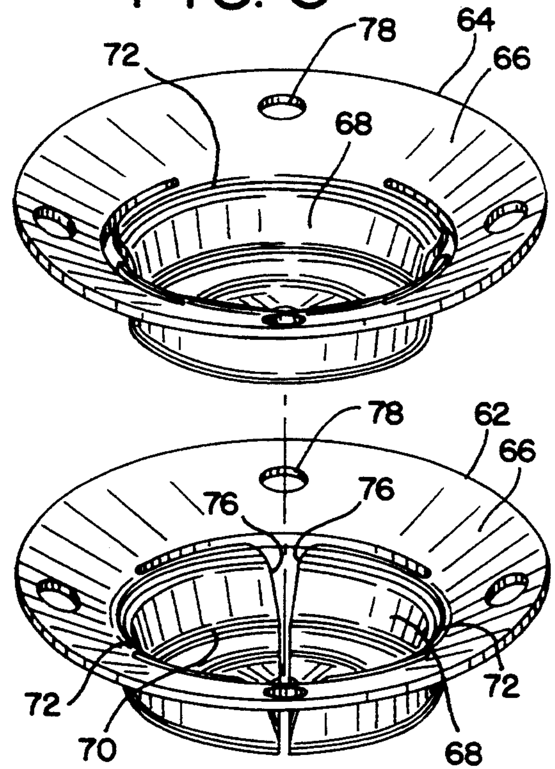
FIG. 6 is an exploded perspective view of the outer and inner protector members of the seal/protector assembly shown in FIG. 2.
Figure 7:
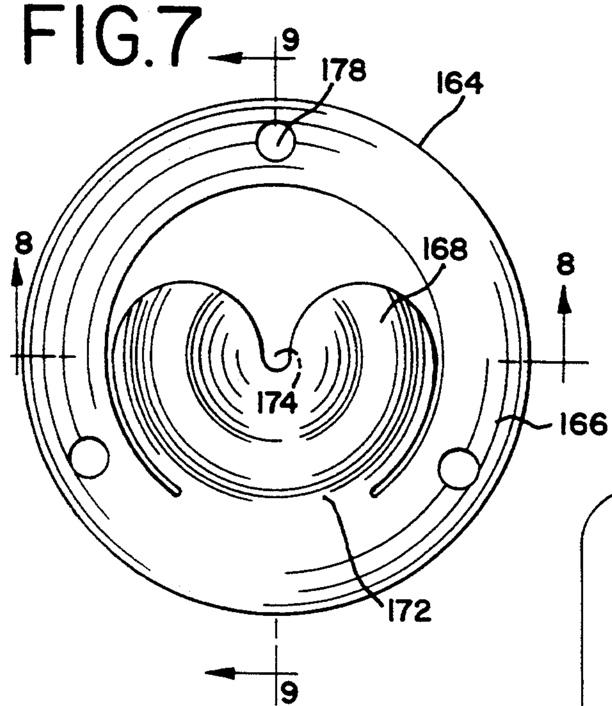
FIG. 7 is a top plan view of an outer protector member used in an alternative embodiment of a seal/protector assembly constructed in accordance with the invention.
Figure 8:
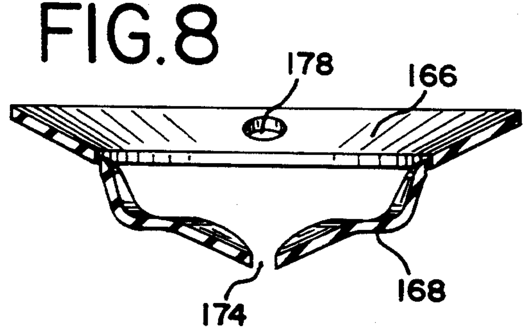
FIG. 8 is a cross-sectional view taken along line 8—8 in FIG. 7.
Figure 9:
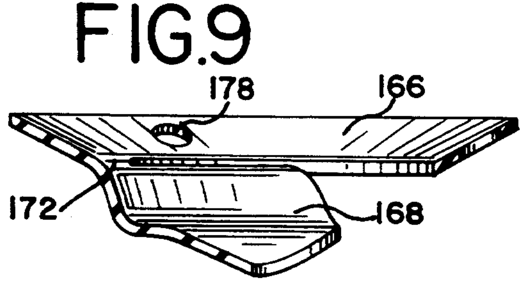
FIG. 9 is a cross-sectional view taken along line 9—9 in FIG. 7.
Figure 10:
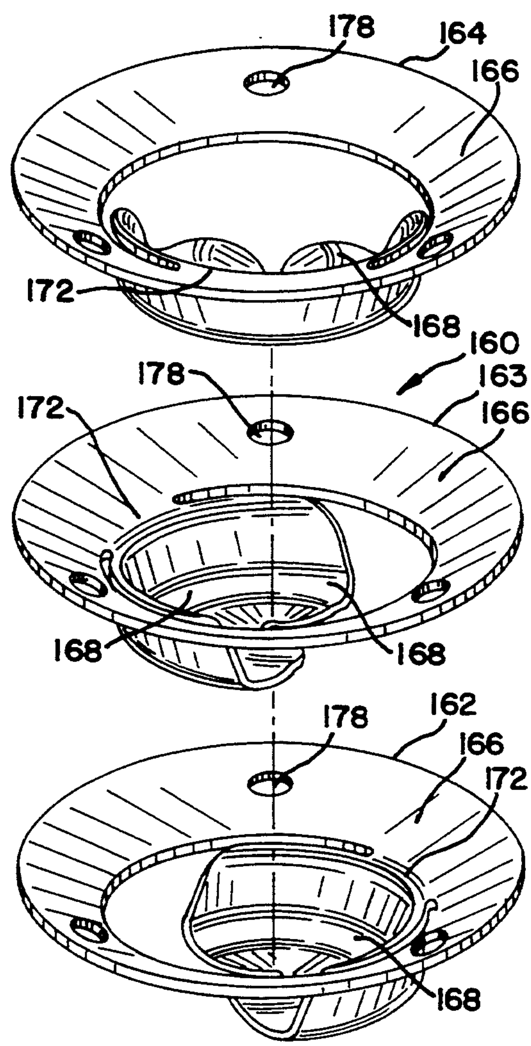
FIG. 10 is an exploded perspective view of the outer, intermediate, and inner protector members of a seal/-protector assembly embodiment that includes a plurality of protector members as shown in FIGS. 7-9.
Figure 11:
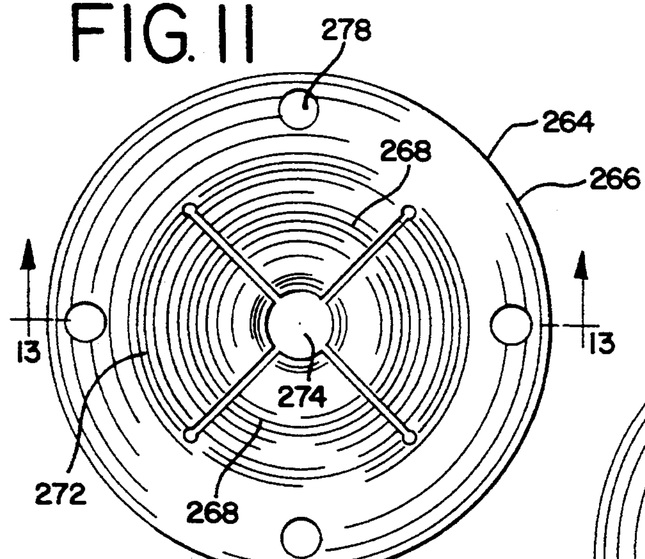
FIG. 11 is a top plan view of an outer protector member used in another alternative embodiment of a seal/-protector assembly constructed in accordance with the invention.
Figure 12:
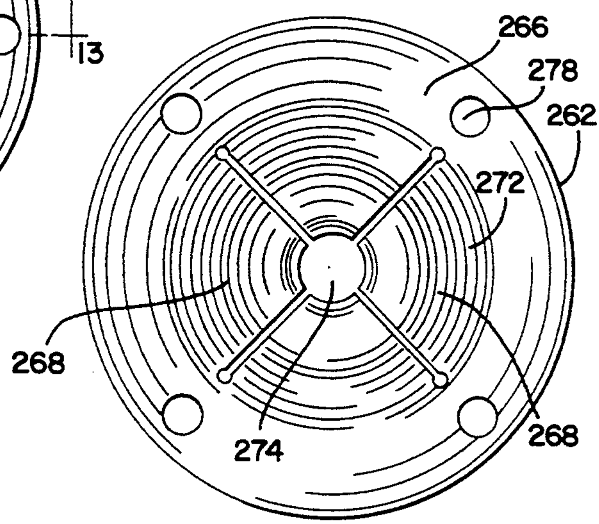
FIG. 12 is a top plan view of an inner protector member that cooperates with the outer protector member shown in FIG. 11.
Figure 13:
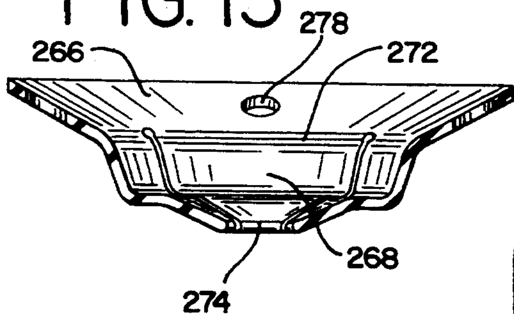
FIG. 13 is a cross-sectional view taken along line 13—13 in FIG. 11.
Figure 14:
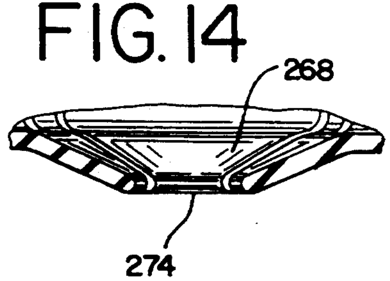
FIG. 14 is an enlarged cross-sectional view of a central portion of the protector member shown in FIG. 13.
Figure 15:
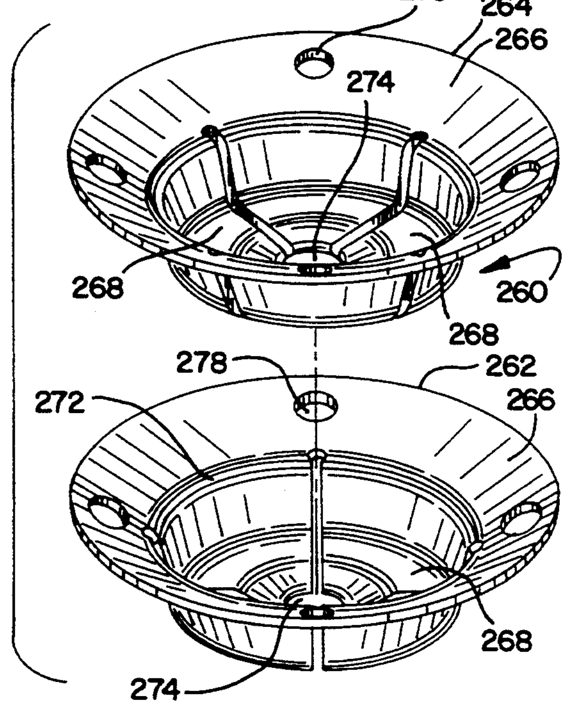
FIG. 15 is an exploded perspective view of the seal/-protector assembly embodiment that includes an outer protector member as shown in FIG. 11 and an inner protector member as shown in FIG. 12.

As best seen in FIG. 6, the leaf portions 68 and 70 of the inner protector member 62 are oriented with respect to the leaf portions 68 and 70 of the outer protector member 64 so that they are not in axial alignment with one another. In this particular embodiment, the portions of the inner protector member are oriented approximately 90 degrees from the leaf portions of the outer protector member. Each of the leaf portions is of a generally concave configuration and define an inner edge 76 that is parallel and immediately adjacent the inner edge 76 of the other leaf portion.

Figure 2:
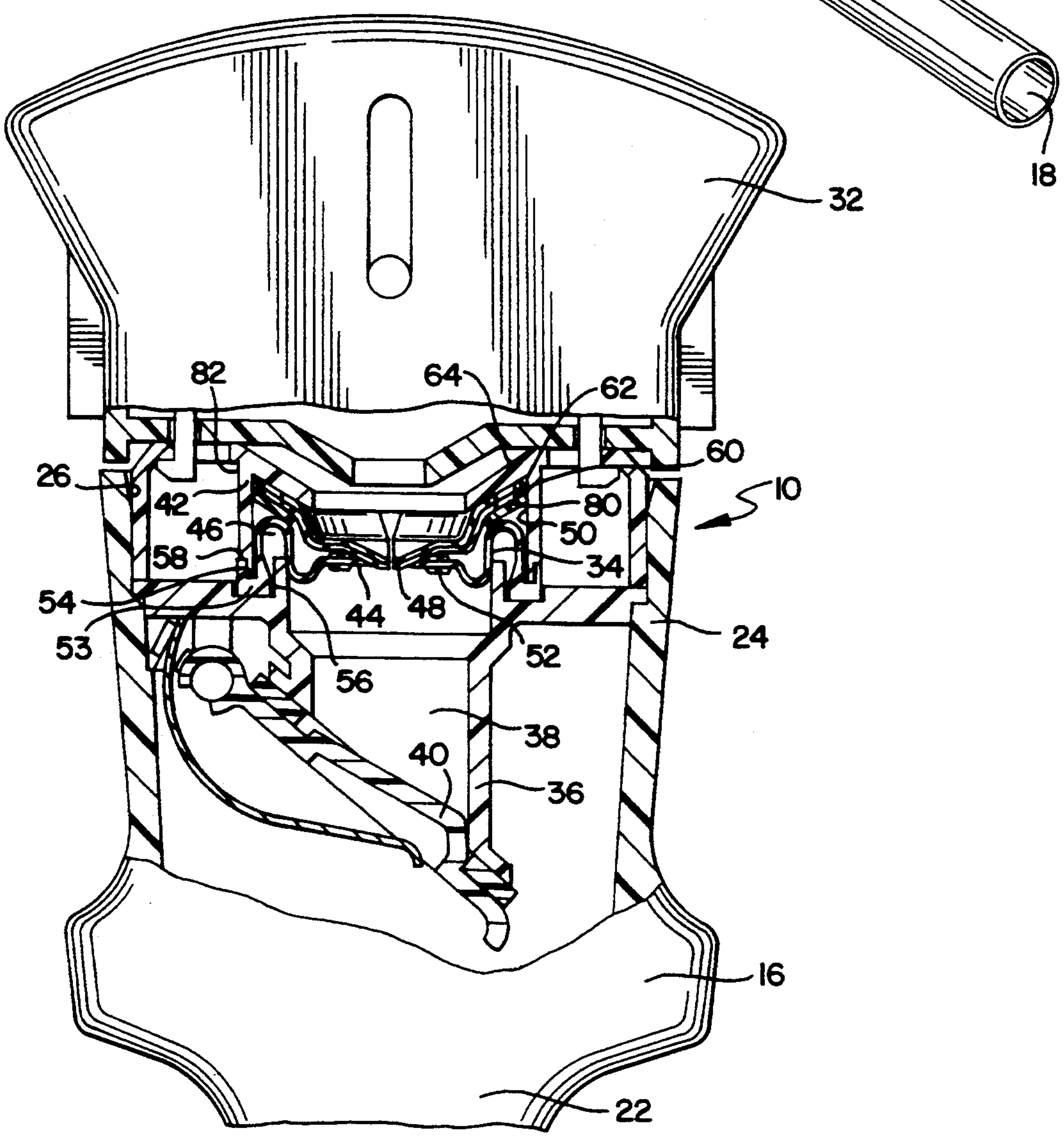
FIG. 2 is an enlarged elevational view, partially in cross-section, of the trocar assembly device shown in FIG. 1, with the obturator fully extended into the trocar tube and a portion of the obturator removed, showing a preferred embodiment of a seal/protector assembly constructed in accordance with the invention.
Figure 3:
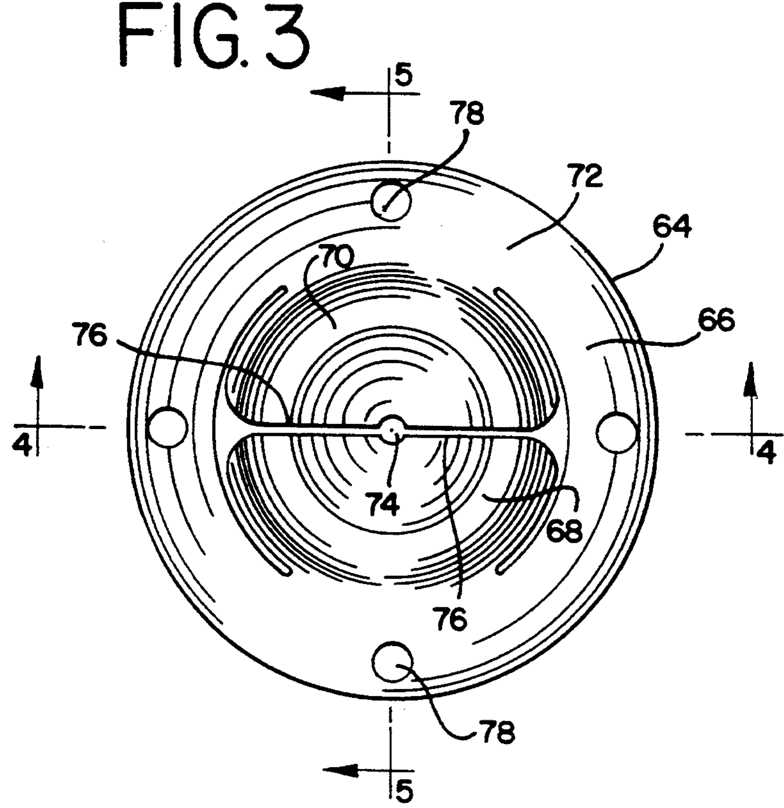
FIG. 3 is an enlarged top plan view of the outer protector member of the protector assembly shown in FIG. 2.
Figure 4:
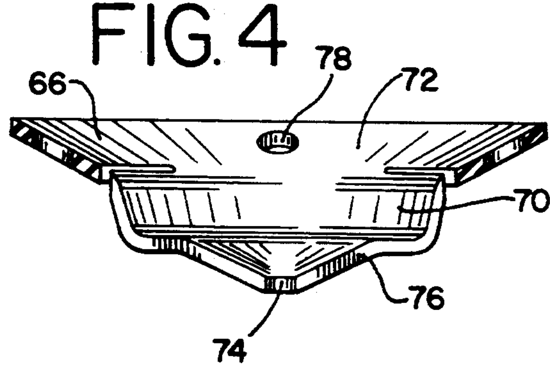
FIG. 4 is a cross-sectional view taken along line 4—4 in FIG. 3.
Figure 5:
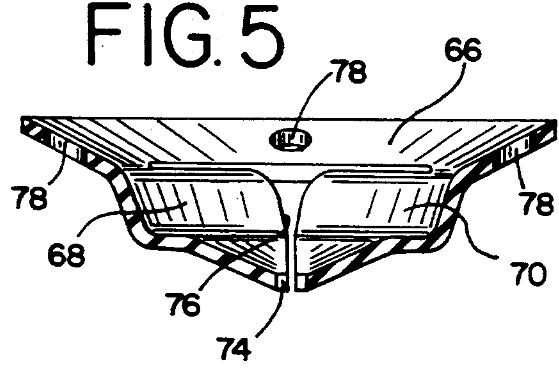
FIG. 5 is a cross-sectional view taken along line 5—5 in FIG. 3.

The collar portions 66 of the protector members are formed with a plurality of spaced apart openings 78. Referring to FIG. 2, the guide/retainer member 42 is formed with distally extending mounting pins 80 that extend through the openings 78 and are preferably secured to the protector members in a suitable manner such as by sonic welding or the like. The openings 78 may alternatively be elongated in a radial direction, and the pins 80 not secured thereto, so as to permit limited distal movement of the protector members within the housing. This allows for a floating movement in the distal direction as an instrument is inserted to provide more protector material at the opening in the seal member when it is fully elongated. An annular spacer ring 82 may be positioned between the inner protector member 62 and the seal member 34. Protector members 62 and 64 are preferably made from a rigid or semi-rigid plastic material, having a low coefficient of friction and a recovery property to permit the leaves to return to their unstressed position, such as a thermoplastic elastomer or a polyurethane elastomer.

Referring to FIGS. 7–10, there is shown an alternative tri-leaf embodiment of the seal/protector assembly 160 that includes an inner protector member 162, an intermediate protector member 163 and an outer protector member 164. Protector members 160, 163 and 164 are of substantially identical construction except for the orientation of the mounting openings formed in the collar portions. The protector members include an annular collar portion 166 and a single concave leaf portion 168 formed integrally with the collar portion so as to form a living hinge portion 172 about which the leaf portion is able to pivot distally and proximally. The leaf portion occupies a substantial portion of the area defined within the collar portion, preferably about two-thirds of such area.

The leaf portions 168 have an opening or open area 174 formed therein in axial alignment with the opening 48 formed in the seal member 34. The leaf portions associated with the protector members 162, 163 and 164 are oriented with respect to one another so as to close the area defined within the collar portions except for the open area 174. An inserted elongate member contacts the leaf portions and causes them to pivot distally increasing the size of the open area 174 to permit the instrument to pass therethrough and then through the opening in the seal member without causing damage to the seal member. As discussed above, the distally moving leaf portions contact the seal member causing the opening formed therein to dilate and increase in diameter.

The collar portions 166 are formed with openings 178. The orientation of the openings 178 with respect to the leaf portions 168 of each of the protector members is such that they are oriented approximately 120 degrees with respect to one another. The protector members 162, 163 and 164 are mounted in the trocar housing in cooperation with a seal member in a similar manner as discussed above with respect to the embodiment shown in FIGS. 2-6.

Referring to FIGS. 11-15, there is shown another alternative embodiment of the seal/protector assembly 260 that is of similar design to the configuration shown in FIGS. 3-6, with the exception that the protector members include four leaf portions. The seal/protector assembly includes an inner protector member 262 and an outer protector member 264. Protector members 262 and 264 are of substantially identical construction except for the orientation of the mounting openings in the collar portions. The protector members include an annular collar portion 266 and four generally pie-shaped leaf portions 268 formed integrally with the collar portion so as to form living hinge portions 272 about which the leaf portions are able to pivot distally and proximally. Each leaf portion occupies approximately one-fourth of the area defined within the collar portion.

The leaf portions 268 define an opening or open area 274 formed therein in axial alignment with the opening 48 formed in the seal member 34. The leaf portions associated with the protector members 262 and 264 are oriented with respect to one another so that they are not in axial alignment with one another. The leaf portions of the inner protector member are oriented approximately 45 degrees from the leaf portions of the outer protector member. An inserted elongated member contacts the leaf portions and causes them to pivot distally increasing the size of the opening 274 to permit the instrument to pass therethrough and then through the opening in the seal member without causing damage to the seal member. Distal movement of the leaf portions causes the opening in the seal member to dilate and increase in diameter in a similar manner as discussed hereinabove.

The collar portions 266 are formed with openings 278. The orientation of the openings 278 in each protector member is approximately 90 degrees with respect to one another. The openings in the inner protector member 262 are generally in alignment with the radial edges of the leaf portions and the openings in the outer protector member 264 are located between the radial edges of the leaf portions. The protector members 262 and 264 are mounted in the trocar housing in a similar manner as discussed above with respect to the embodiment shown in FIGS. 2-6.

Figure 16:
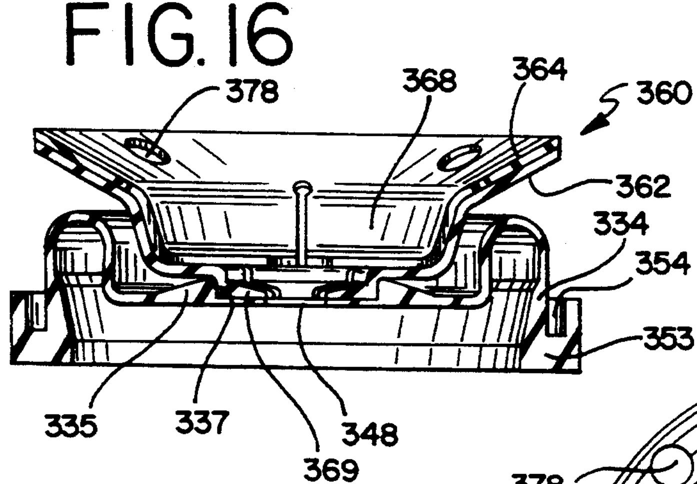
FIG. 16 is a cross-sectional view of another alternative embodiment of a seal/protector assembly constructed in accordance with the invention.
Figure 17:
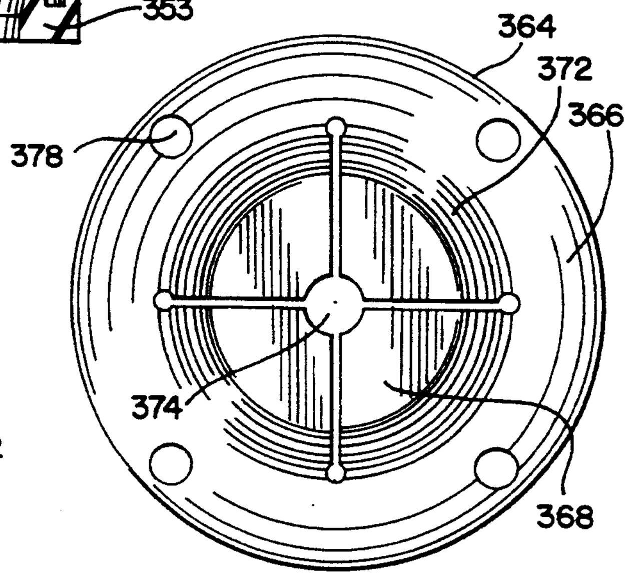
FIG. 17 is a top plan view of the outer protector member of the seal/protector assembly shown in FIG. 16.
Figure 18:
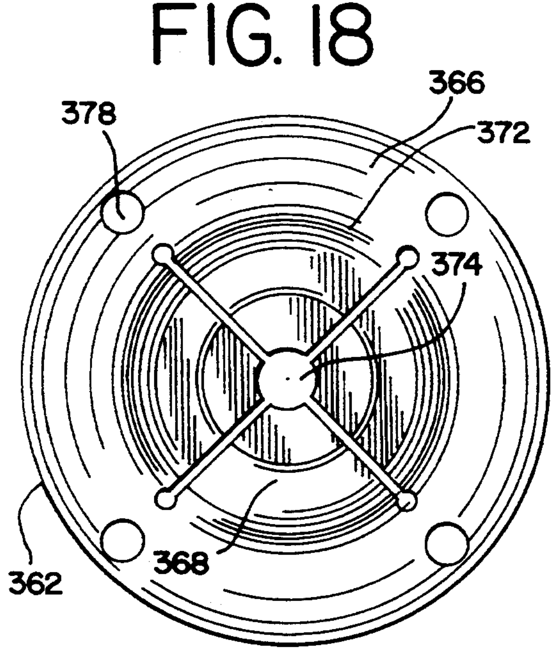
FIG. 18 is a top plan view of the inner protector member of the seal/protector assembly shown in FIG. 16.
Figure 19:
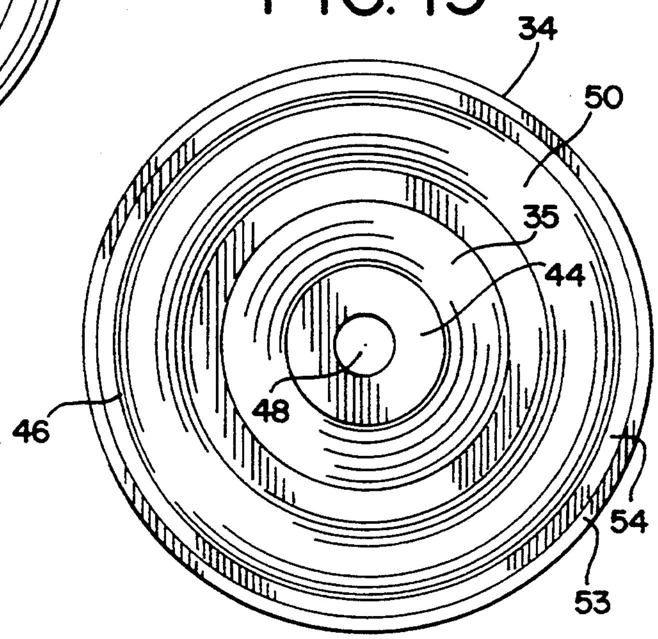
FIG. 19 is a top plan view of the seal member shown in FIG. 16.

Referring to FIGS. 16-19, there is shown another alternative embodiment of the invention that includes a seal/protector assembly 360 that interlocks with the seal member 334. The outer surface of the seal member 334 is formed with an outwardly extending annular ramp portion 335 defining a recess portion 337. The seal/protector assembly 360 includes an inner protector member 362 and an outer protector member 364. Outer protector member 364 is of similar configuration to outer protector member 264 discussed above. Inner protector member 362 is of similar configuration to outer protector member 262 discussed above except that the inner sections of the leaf portions 368 define an inwardly extending annular section 369 that is received in recess portion 337, as best seen in FIG. 16. The portions of the protector members 362 and 364 that correspond to similar portions of the protector members 262 and 264 are identified in FIGS. 16-19 with reference numerals having the same last two digits.

An inserted elongate member contacts the leaf portions 368 causing them to pivot distally increasing the size of the open area 374 to permit the instrument to pass therethrough and then through the opening in the seal member. The distally moving leaf portions 368 associated with the inner protector member 362 are already in contact with the seal member to facilitate the initial dilation of the opening in the seal member. Continued distal movement of the leaf portions causes the annular section 369 to be withdrawn from the recess portion 337 of the seal member. The seal member 334 and the protector members 362 and 364 are mounted in the trocar housing in a similar manner as discussed above with respect to the embodiment shown in FIGS. 2-6.

Figure 27:
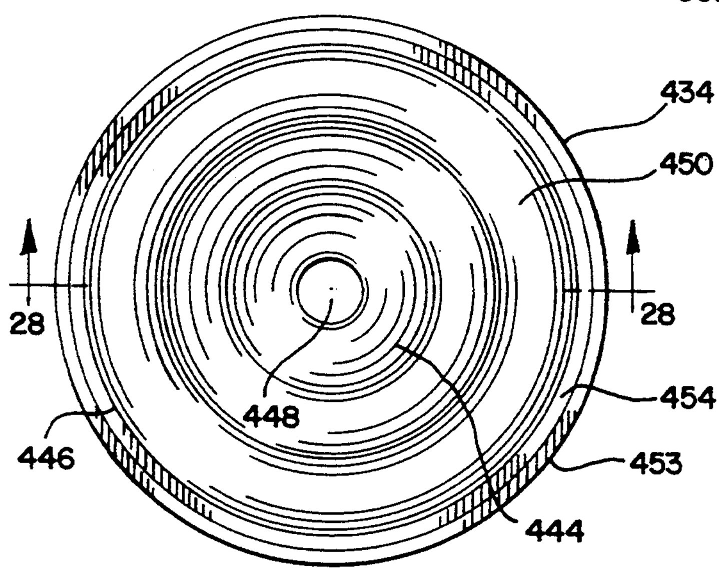
FIG. 27 is a top plan view of a seal member intended for use in cooperation with the seal/protector assemblies that utilize protector members as shown in FIGS. 20-21 and 24-26.
Figure 28:
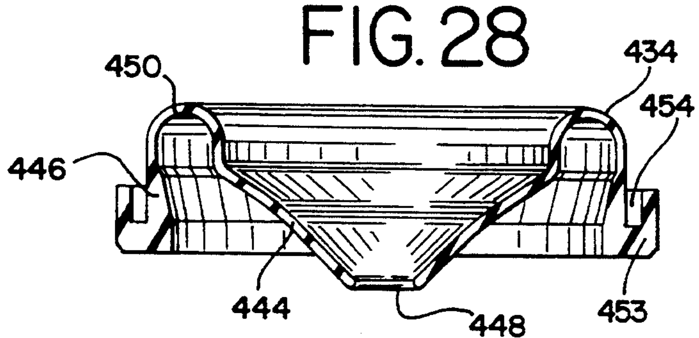
FIG. 28 is a cross-sectional view taken along line 28—28 in FIG. 27.

Referring to FIGS. 27 and 28, there is shown an alternative funnel-shaped embodiment of the seal member identified by the reference numeral 434. Seal member 434 and the above discussed seal member 34 are of similar construction except for differences in the configuration of the inner sections thereof. The portions of seal member 434 that correspond to the portions of seal member 34 are identified with a reference numeral having the same last two digits. Reference is made to the above discussion of the portions of seal member 34 that correspond to the portions of seal member 434. The inner portion 444 of seal member 434 is funnel-shaped as shown in FIG. 28.

Figure 20:
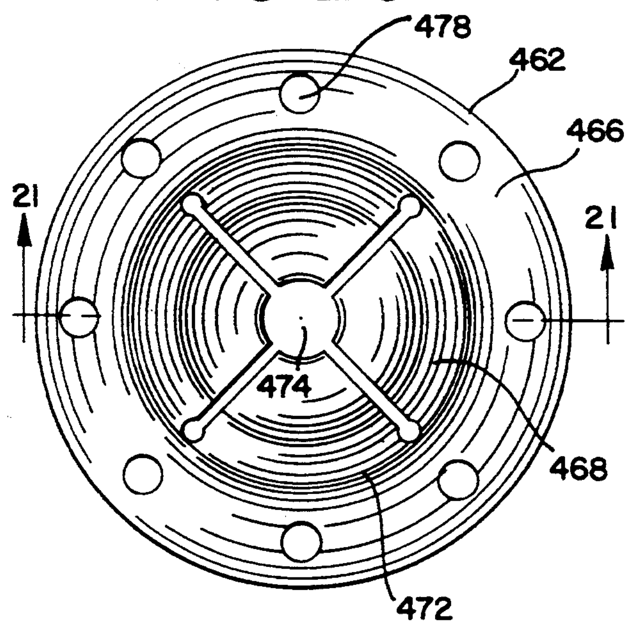
FIG. 20 is a top plan view of another alternative embodiment of a protector member constructed in accordance with the invention.
Figure 21:
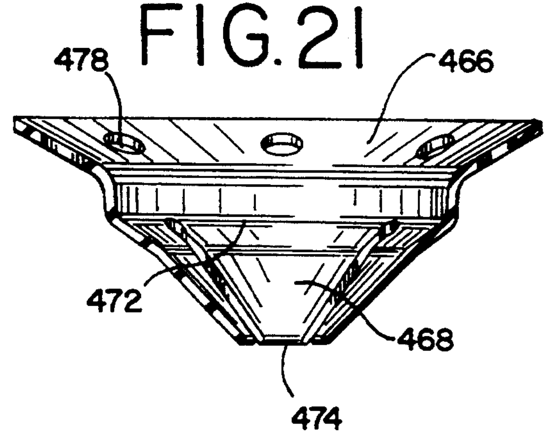
FIG. 21 is a cross-sectional view taken along line 21—21 in FIG. 20.

A seal/protector assembly, for use in cooperation with the seal member 434, is shown in FIGS. 20-21, and includes an inner protector member 462 and an outer protector member (not shown). The inner and outer protector members are of the same construction. Protector member 462 is of similar configuration to protector member 262 except that there are additional openings 478 formed in the collar portion 466 and the shape of the leaf members 468 is such as to form a funnel shape that cooperates with the inner portion 444 of seal member 434. The additional openings 478 permit the same protector member to be utilized as the inner and outer protector members, one oriented 45 degrees with respect to the other. The seal member 434 and the inner and outer protector members are mounted in the trocar housing and function in a similar manner as discussed above.

Figure 22:
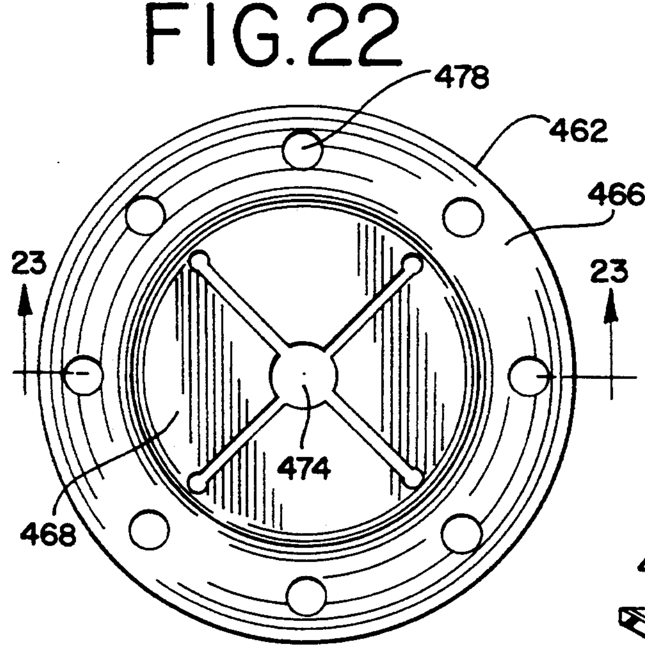
FIG. 22 is a top plan view of a further alternative embodiment of a protector member constructed in accordance with the invention.
Figure 23:
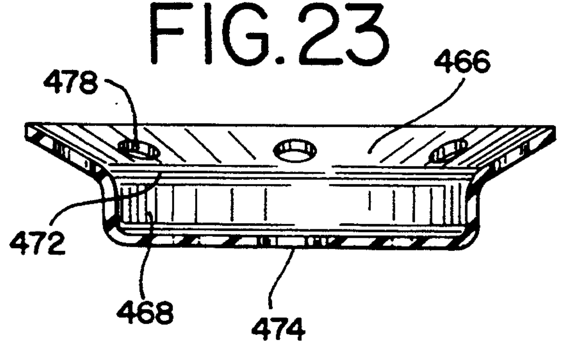
FIG. 23 is a cross-sectional view taken along line 23—23 in FIG. 22.

Referring to FIGS. 22–23, a protector member is shown that is similar in design to protector member 462 except that it has flat leaf portions 468.

Figure 24:
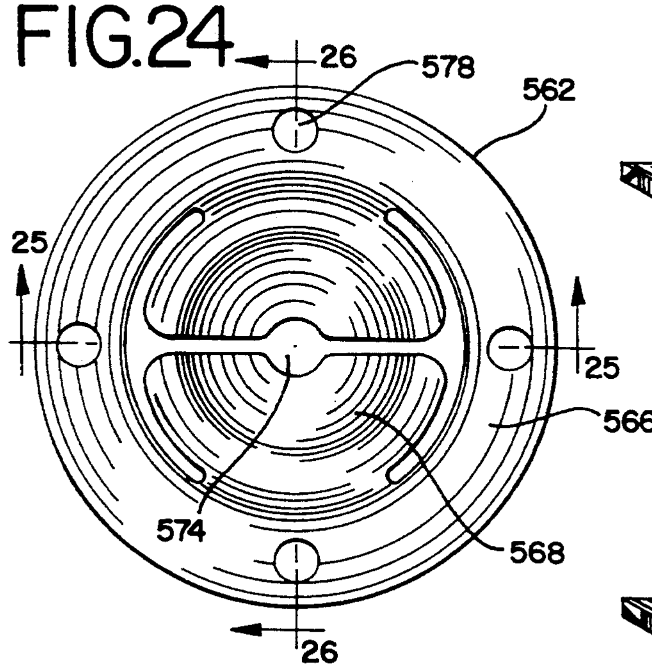
FIG. 24 is a top plan view of an alternative embodiment of a protector member constructed in accordance with the invention.
Figure 25:
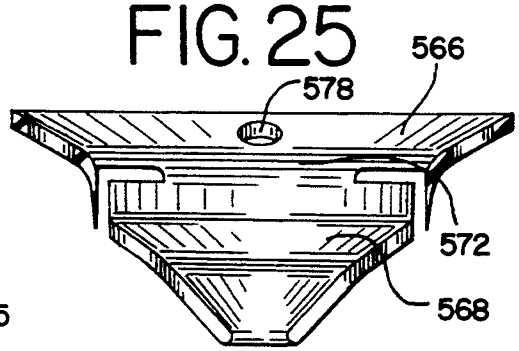
FIG. 25 is a cross-sectional view taken along line 25—25 in FIG. 24.
Figure 26:
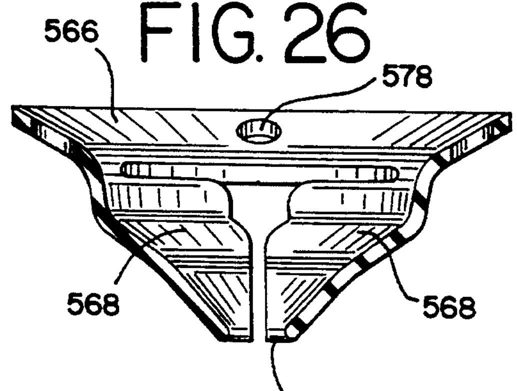
FIG. 26 is a cross-sectional view taken along line 26—26 in FIG. 24.

Referring to FIGS. 24–26, there is shown another seal/protector assembly for use in cooperation with seal member 434 that includes an inner protector member 562 and an outer protector member (not shown). The construction of the protector members is substantially the same as the construction of protector members 162 and 164. The portions of the protector member 562 that correspond to similar portions of the protector member 162 are identified in FIGS. 24–26 with reference numerals having the same last two digits. The shape of the leaf portions 568 are such as to form a funnel shape that cooperates with the inner portion 444 of seal member 434, as shown in FIG. 28. The seal member 434 and the inner and outer protector members are mounted in the trocar housing and function in a similar manner as discussed above.

Figure 29:
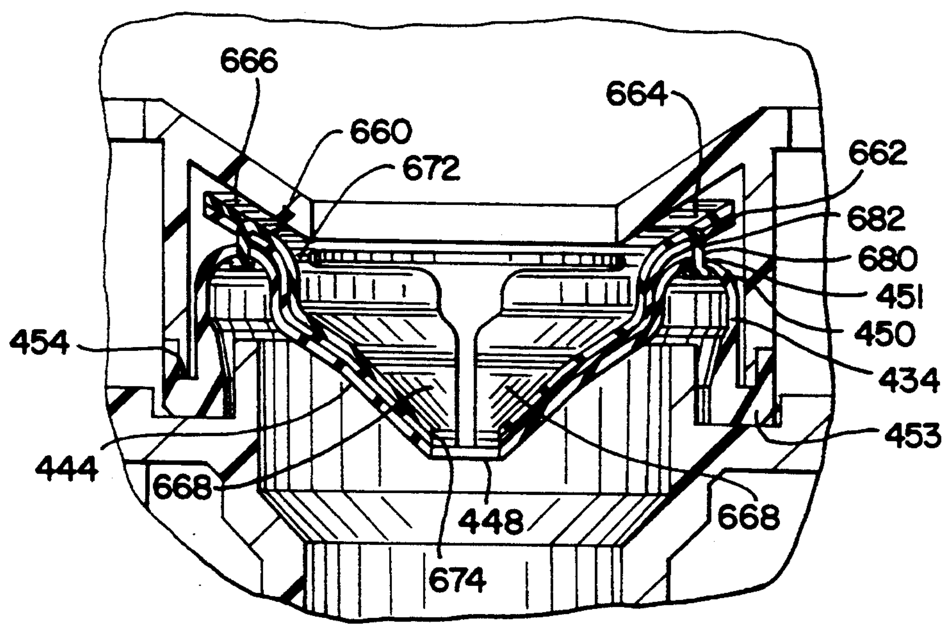
FIG. 29 is a cross-sectional view of a portion of a trocar assembly device showing an alternative embodiment of a seal/protector assembly constructed in accordance with the invention.
Figure 30:
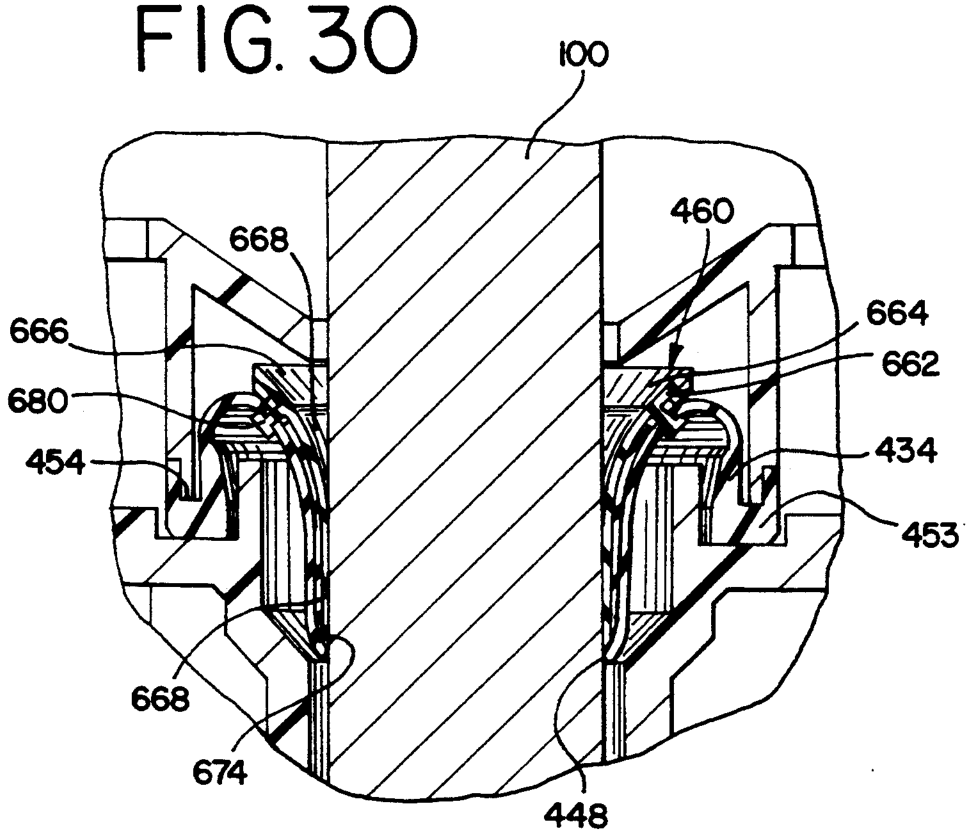
FIG. 30 is a cross-sectional view of the portion of the trocar assembly shown in FIG. 29 with an elongate instrument extending through the seal/protector assembly.

A further alternative embodiment of the invention is shown in FIGS. 29 and 30 which includes a seal/protector assembly 660 that is attached to a seal member 434. Seal member 434 is configured as shown in FIGS. 27 and 28 and discussed above. Protector assembly 660 includes an inner protector member 662 and an outer protector member 664. The construction of protector members 662 and 664 are substantially the same as the construction of protector member 562. The portions of the protector members 662 and 664 that correspond to similar portions of the protector member 562 are identified in FIGS. 29 and 30 with reference numerals having the same last two digits. The outer protector member 664 is formed with a plurality of spaced apart, distally projecting connecting stem portions 680. Stem portions 680 extend through corresponding spaced apart openings 682 formed through inner protector member 662 and spaced apart openings 451 formed in corrugated portion 450 of seal member 434. The distal ends of stem portions 680 are dimensioned so as to retain the stem portions in place and maintain inner protector member 662 in contact with seal member 434. The seal member 434 and the inner and outer protector members 662 and 664 are mounted in the trocar housing in a similar manner as discussed above with respect to FIG. 2.

Referring to FIG. 30, there is shown an elongate instrument member 100 inserted through the protector assembly 660 and the seal member 434. As elongate member 100 contacts the leaf portions 668 they are caused to pivot distally increasing the size of the open area 674 to permit the elongate member to pass therethrough and then through the opening in the seal member. The distally moving leaf portions contact the seal member causing the opening 448 formed therein to dilate and increase in diameter. The attachment of the protector assembly to the seal member causes the protector member to move with the seal member to increase the range of sealing during off-centered insertion of elongated instruments.

Figure 31:
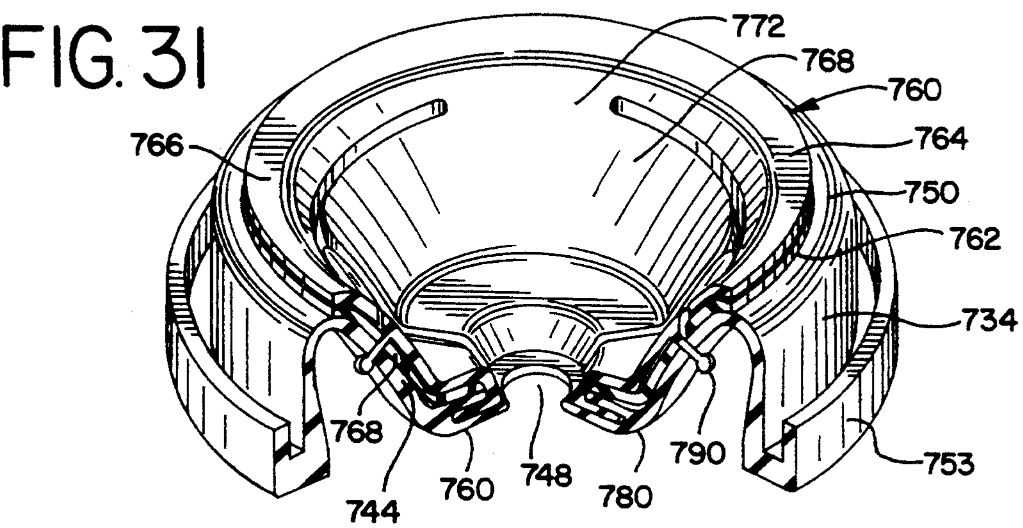
FIG. 31 is a perspective view of a seal/protector assembly, partially broken away in cross-section, showing an alternative embodiment of the invention.
Figure 32:
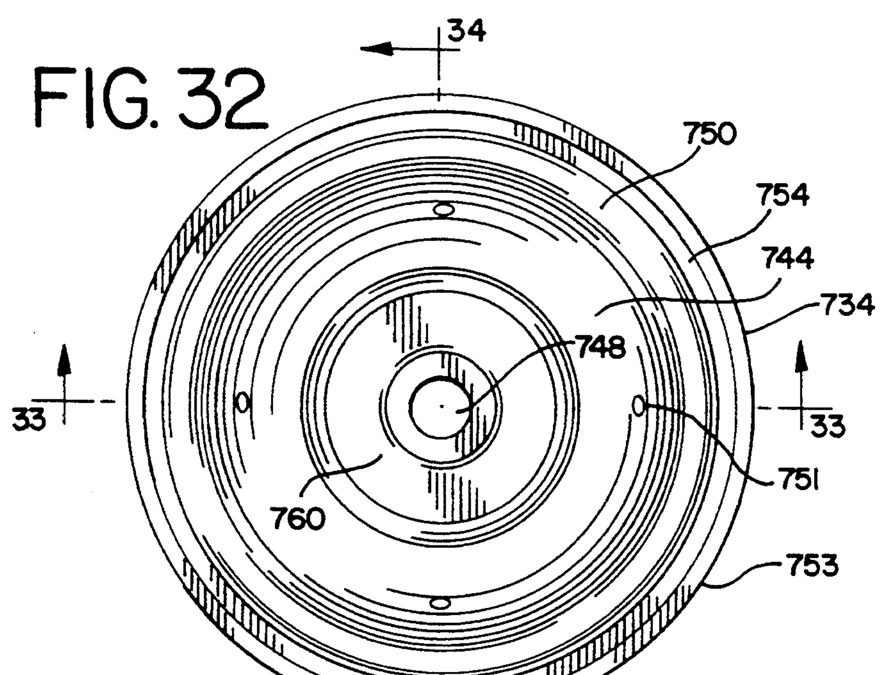
FIG. 32 is a top plan view of the seal member of the seal/protector assembly shown in FIG. 31.
Figure 33:
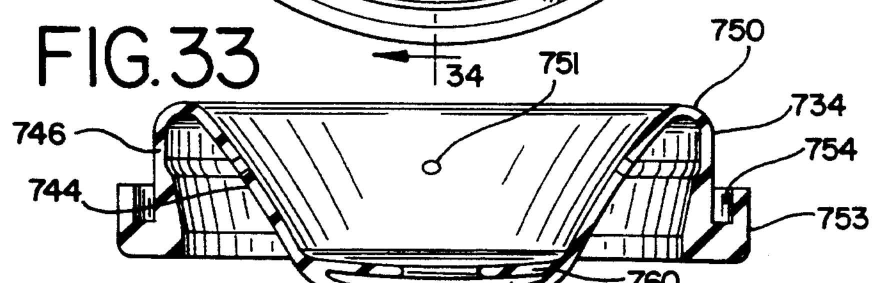
FIG. 33 is a cross-sectional view taken along line 33—33 in FIG. 32.
Figure 34:
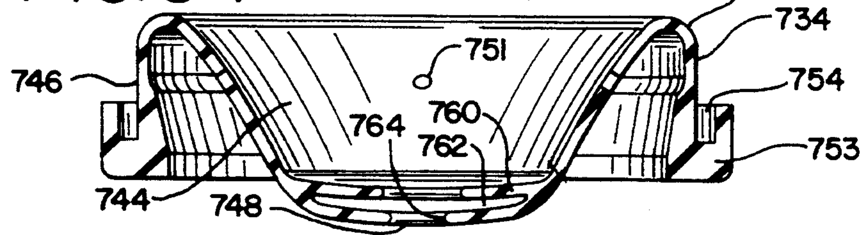
FIG. 34 is a cross-sectional view taken along line 34—34 in FIG. 32.

Another alternative embodiment of the invention is shown in FIGS. 31–39, which includes a protector assembly 760 that is attached to a cooperating seal member 734. Referring to FIGS. 32–34, seal member 734 is of similar construction to seal members 34 and 434 except for differences in the shape and configuration of the inner sections thereof. The portions of seal member 734 that correspond to the portions of seal members 34 and 434 are identified with a reference numeral having the same last two digits. Reference is made to the above discussions of the portions of seal members 34 and 434 that correspond to the portions of seal member 734. The inner section 744 of seal member 734 is formed with an inwardly extending annular flange 760 that defines a cavity 762. The inner section 744 is formed with spaced apart openings 751.

Figure 35:
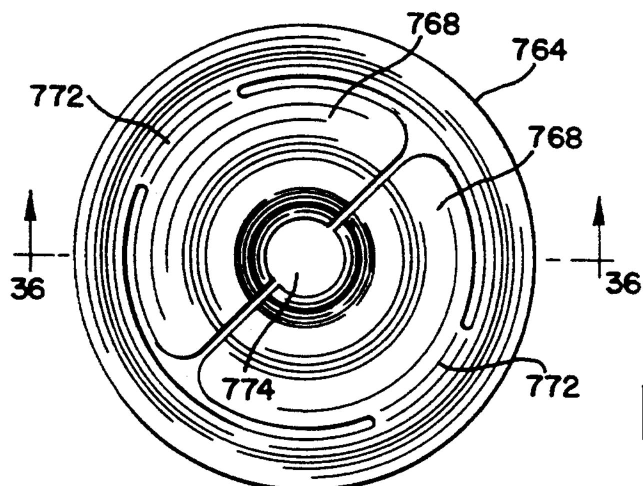
FIG. 35 is a top plan view of the outer protector member of the seal/protector assembly shown in FIG. 31.
Figure 39:
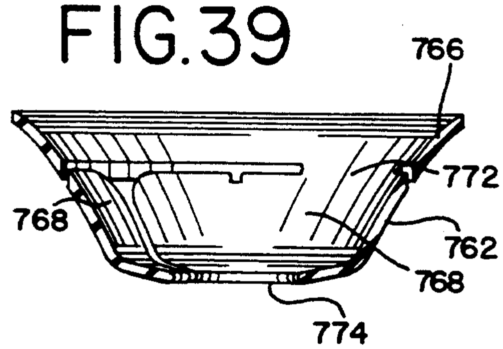
FIG. 39 is a cross-sectional view taken along line 39—39 in FIG. 38.
Figure 36:
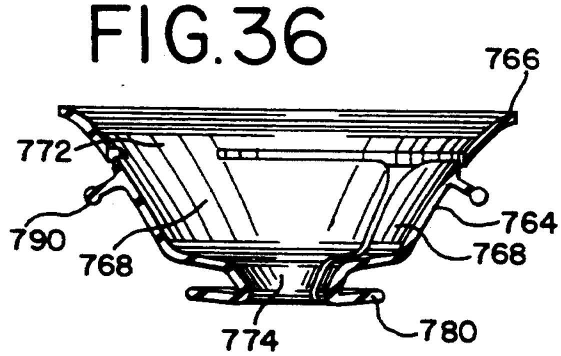
FIG. 36 is a cross-sectional view taken along line 36—36 in FIG. 35.
Figure 38:
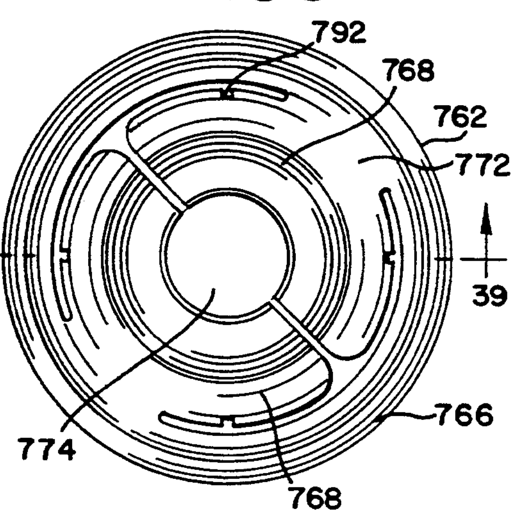
FIG. 38 is a top plan view of the inner protector member of the seal/protector assembly shown in FIG. 31.
Figure 37:
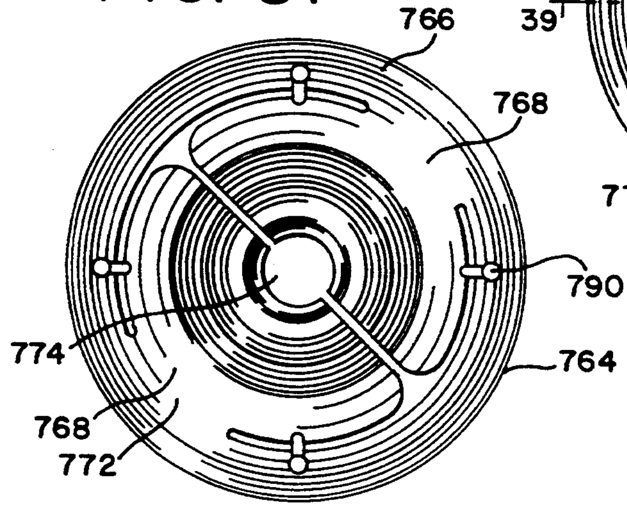
FIG. 37 is a bottom plan view of the outer protector member shown in FIG. 35.
Figure 40:
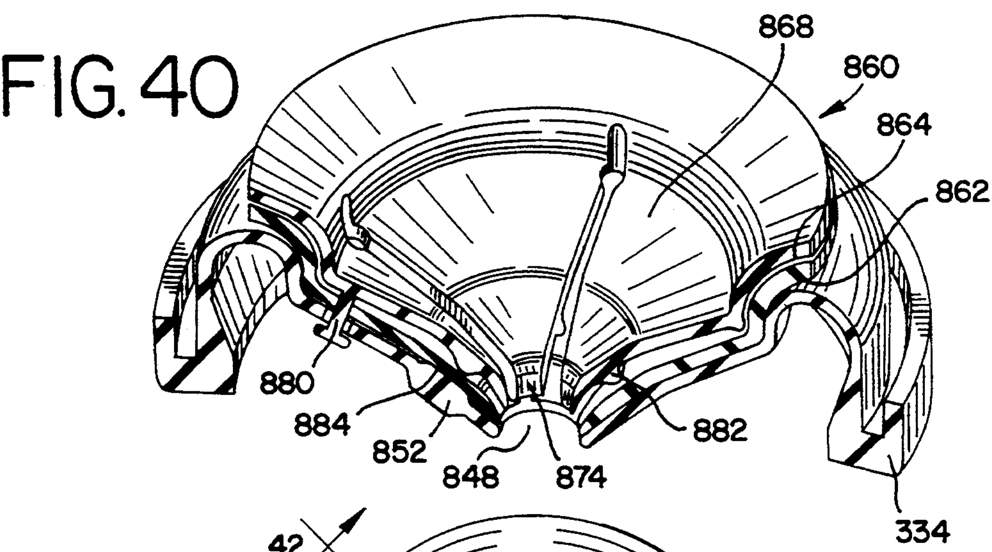
FIG. 40 is a perspective view of a seal/protector assembly, partially broken away in cross-section, showing an alternative embodiment of the invention.
Figure 41:
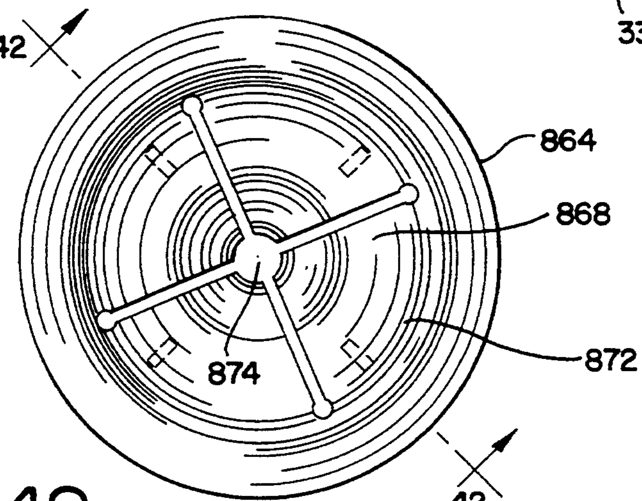
FIG. 41 is a top plan view of the outer protector member of the seal/protector assembly shown in FIG. 40.
Figure 42:
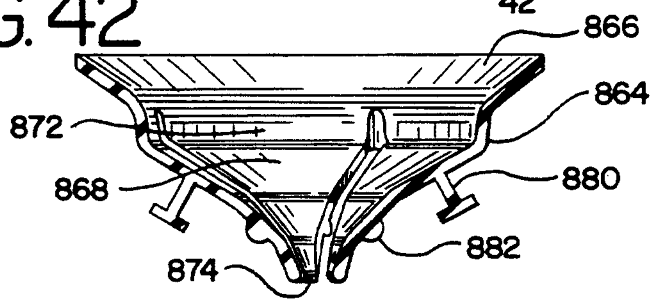
FIG. 42 is a cross-sectional view taken along line 42—42 in FIG. 41.
Figure 43:
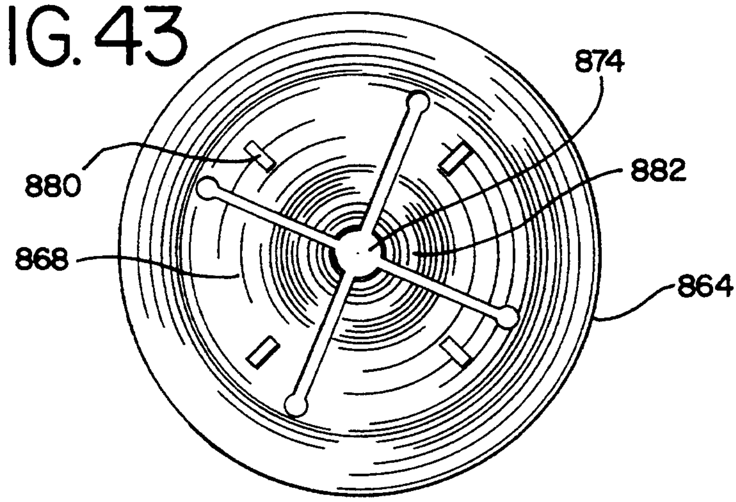
FIG. 43 is a bottom plan view of the outer protector member shown in FIG. 41.

Protector assembly 760 includes an inner protector member 762 and an outer protector member 764. Referring to FIGS. 35–37, outer protector member 764 includes a collar portion 766 and a pair of leaf portions 768 that pivot about hinge portions 772 in a similar manner as discussed above. The leaf portions 768 define an opening 774. The inner section of the leaf portions 768 extend distally and then outwardly defining a flange portion 780, as best seen in FIG. 36. Referring to FIGS. 38 and 39, inner protector member 762 includes a collar portion 766 and a pair of leaf portions 768 that pivot about hinge portions 772. The leaf portions 768 associated with protector member 762 define an opening 774 that is larger in diameter than the corresponding opening 774 in protector member 764.

As seen in FIG. 31, the protector assembly 60 is assembled by extending the flange portion 780 of outer protector member 764 through the opening 774 in inner protector member 762 such that the distal edges of the leaf portions 768 of the inner protector member are positioned between flange portion 780 and the leaf portions 768 of the outer protector member. The protector assembly 760 is attached to the seal member 734 by positioning the flange portion 780 of outer protector member 762 in cavity 762 of the seal member 734.

In accordance with a preferred embodiment of the invention, the outer protector member 764 is formed with a plurality of spaced apart, distally projecting connecting stem portions 790. Stem portions 790 extend through corresponding spaced apart openings 792 formed through inner protector member 762 and spaced apart openings 751 formed inner section 744 of seal member 734. The distal ends of stem portions 790 are dimensional so as to retain the stem portions in place and maintain inner protector member 762 in contact with seal member 734. The seal member 734 and the inner and outer protector members 762 and 764 are mounted in the trocar housing in a similar manner as discussed above with respect to FIG. 2.

In operation of the embodiment shown in FIGS. 31–39, an inserted elongate member contacts the leaf portions 768 and causes them to pivot distally increasing the size of the open area 774 in the outer protector member 764 to permit the elongate member to pass therethrough. The distally moving leaf portions 768 associated with the outer protector member 762 causes the open area 774 in the inner protector member 762 and the opening 248 in seal member 234 to quickly dilate and increase in diameter. The inner edge 764 of the seal member contacts and seals against the elongate member.

Figure 44:
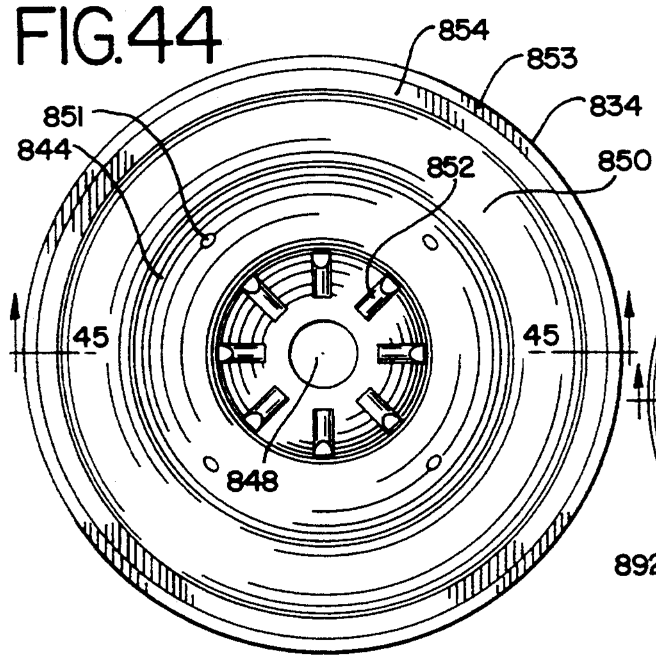
FIG. 44 is a top plan view of the seal member of the seal/protector assembly shown in FIG. 40.
Figure 47:
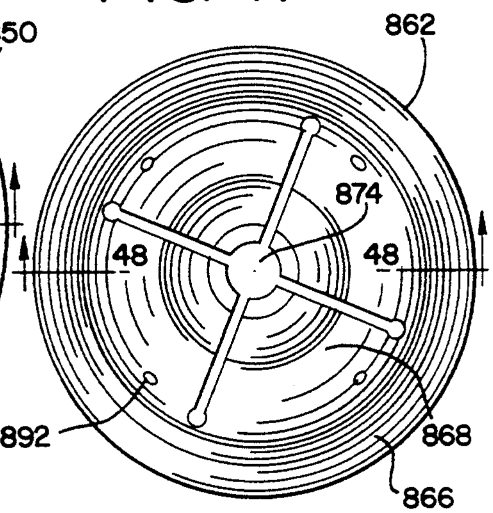
FIG. 47 is a top plan view of the inner protector member of the seal/protector assembly shown in FIG. 40.
Figure 45:
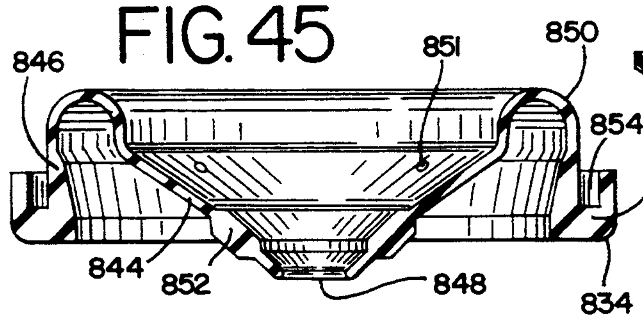
FIG. 45 is a cross-sectional view taken along line 45—45 in FIG. 44.
Figure 48:
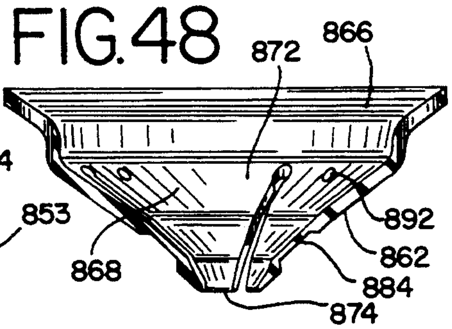
FIG. 48 is a cross-sectional view taken along line 48—48 in FIG. 47.
Figure 46:
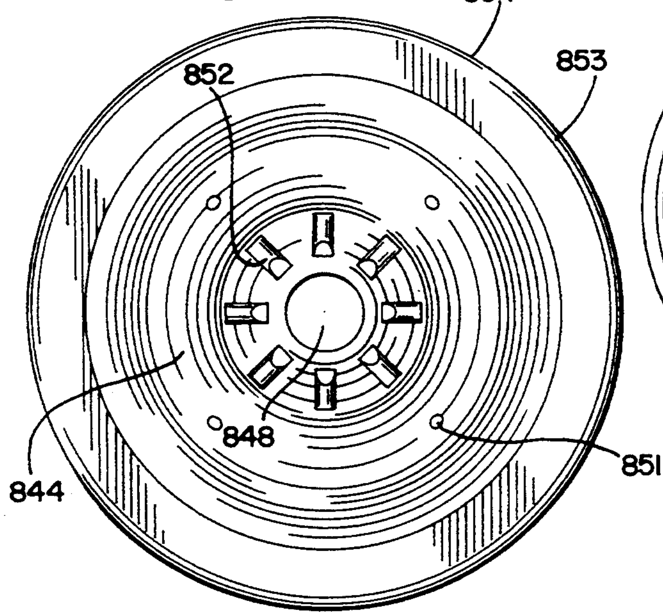
FIG. 46 is a bottom plan view of the seal member shown in FIG. 44.
Figure 49:
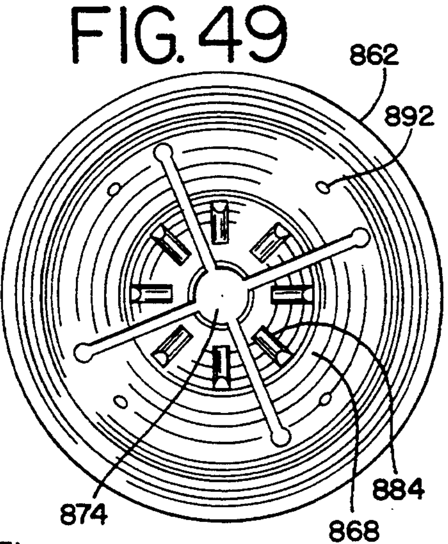
FIG. 49 is a bottom plan view of the inner protector member shown in FIG. 47.
Figure 50:
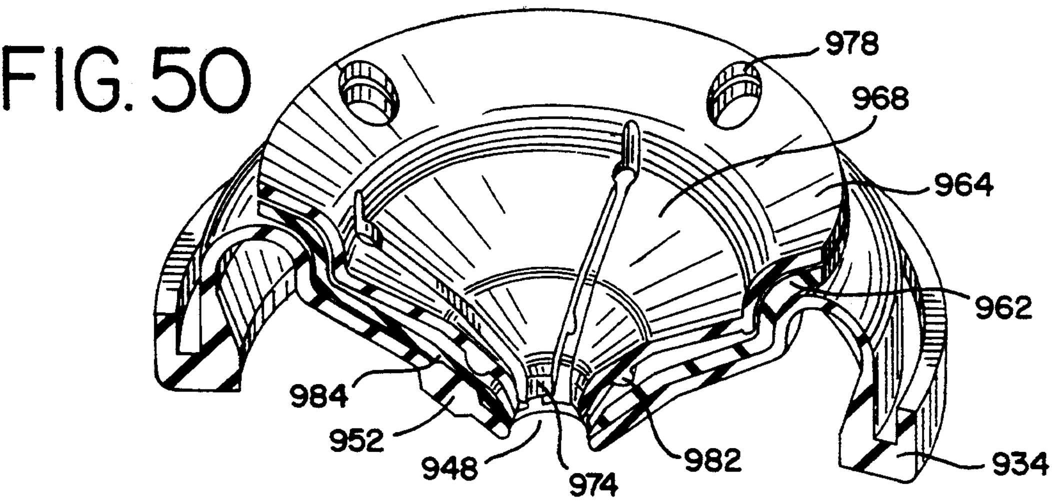
FIG. 50 is a perspective view of a seal/protector assembly, partially broken away in cross-section, showing an alternative embodiment of the invention.
Figure 51:
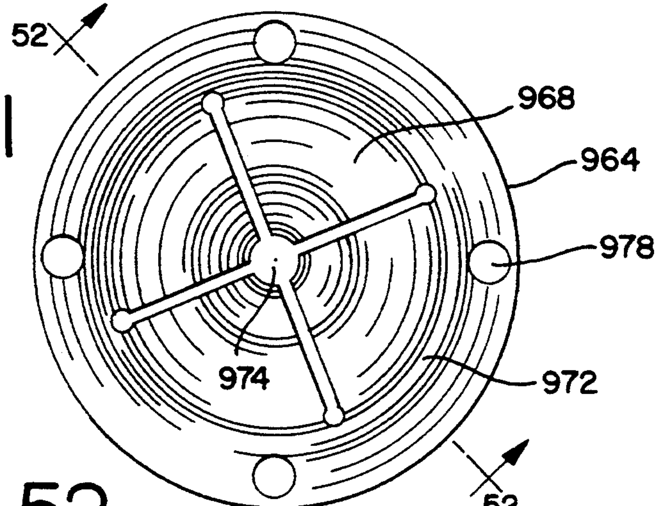
FIG. 51 is a top plan view of the outer protector member of the seal/protector assembly shown in FIG. 50.
Figure 52:
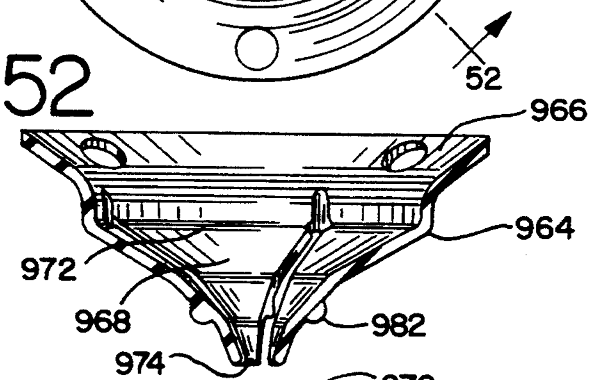
FIG. 52 is a cross-sectional view taken along line 52—52 in FIG. 51.
Figure 53:
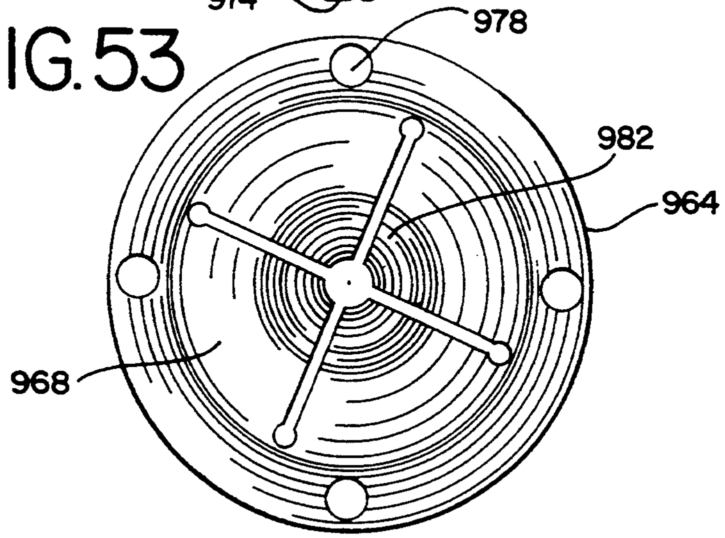
FIG. 53 is a bottom plan view of the protector member of the seal/protector assembly shown in FIG. 50.
Figure 54:
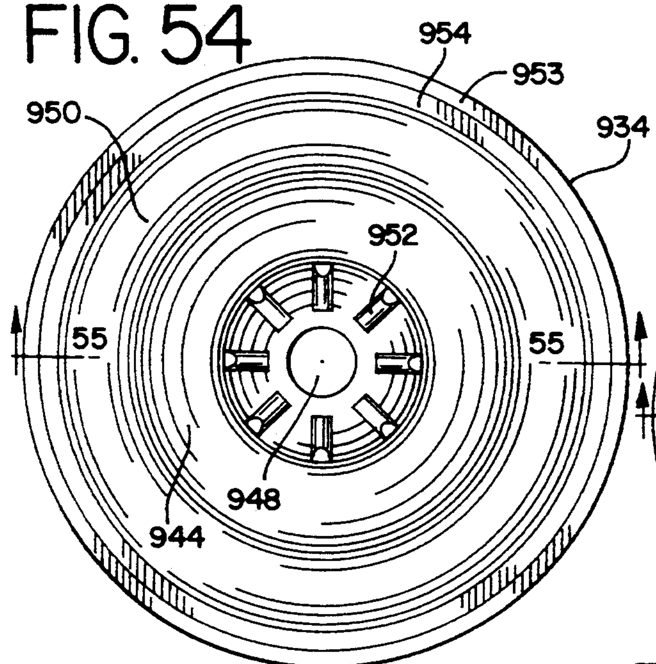
FIG. 54 is a top plan view of the seal member of the seal/protector assembly shown in FIG. 50.
Figure 57:
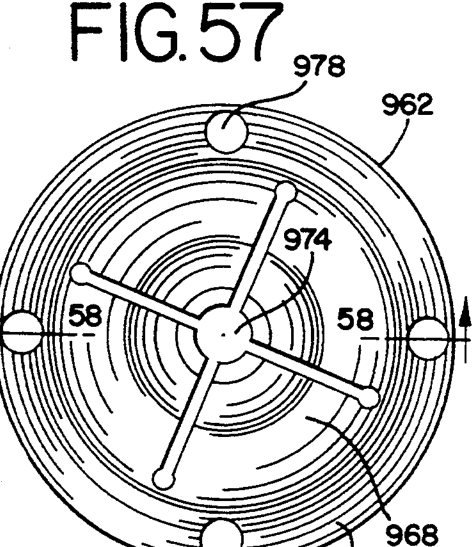
FIG. 57 is a top plan view of the inner protector member of the seal/protector assembly shown in FIG. 50.
Figure 55:
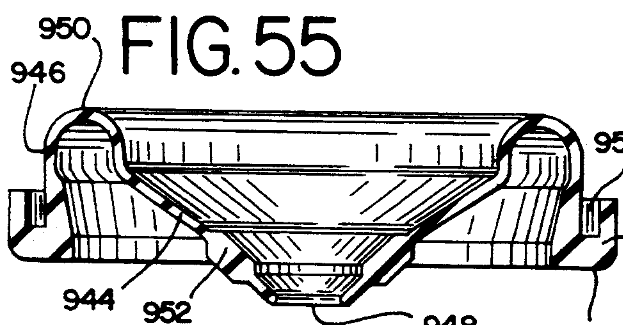
FIG. 55 is a cross-sectional view taken along line 55—55 in FIG. 54.
Figure 58:
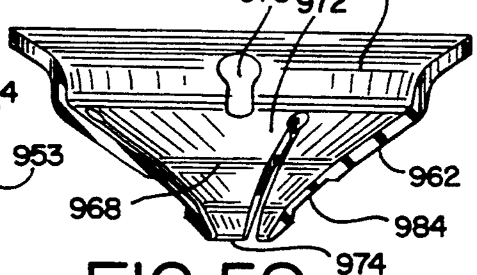
FIG. 58 is a cross-sectional view taken along line 58—58 in FIG. 57.
Figure 56:
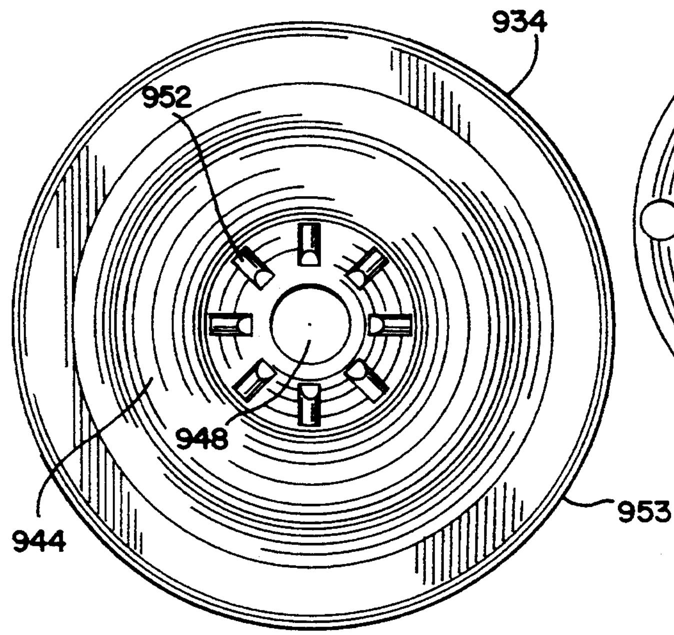
FIG. 56 is a bottom plan view of the seal member shown in FIG. 54.
Figure 59:
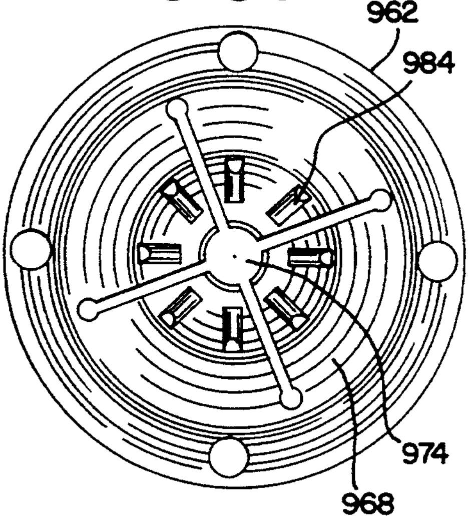
FIG. 59 is a bottom plan view of the inner protector member shown in FIG. 57.

Referring to FIGS. 40–49, there is shown yet another embodiment of the invention which includes a seal/protector assembly 860 that is attached to a seal member 834. Seal member 834 is configured as shown in FIGS. 44–46. Seal member 834 and the above discussed seal member 434 are substantially similar in construction and the common portions thereof are identified with reference numerals having the same last two digits. Seal member 834 is provided with a plurality of spaced apart projections or ribs 852 that extend outwardly from the surface of the seal member and radially with respect to opening 348. Projections 852 are preferably integrally formed in inner section 844.

Seal/protector assembly 860 includes an inner protector member 862 and an outer protector member 864. Except as indicated below, protector members 862 and 864 are similar in construction to protector members 662 and 664. The corresponding portions of these protector members are identified with reference numerals having the same last two digits. The protector members 862 and 864 are each formed with four pie-shaped leaf portions 868. The outer protector member 864 is formed with a plurality of spaced apart, distally projecting connecting stem portions 880. Stem portions 880 are arranged to extend through corresponding spaced apart openings 892 formed through inner protector member 862 and spaced apart openings 851 formed in inner section 844 of seal member 834. The distal ends of stem portions 880 are dimensioned so as to retain the stem portion in place and maintain inner protector member 862 in contact with seal member 834.

In accordance with a feature of this embodiment, the outer protector member 864 is provided with an annular rib portion 882 extending from the inner surface thereof to create a space between outer protector member 864 and the inner protector member 862. The inner protector member 862 is formed with a plurality of spaced apart recess portions 884 for receipt of a corresponding rib 852 therein. The above structure and relationships results in a more rapid dilation of the opening 848 in seal member 834 as an elongate member is directed therethrough.

Referring to FIGS. 50–59, a further embodiment of the invention is shown that is similar in configuration and operation to the embodiment shown in FIGS. 40–49. This embodiment includes a seal member 934 and a seal/protector assembly 960 that includes an inner protector member 962 and an outer protector member 964. Seal member 934 is of similar construction as seal member 834 and protector members 962 and 964 are of similar construction as corresponding protector members 862 and 864. The corresponding portions of these members are identified with reference numerals having the same last two digits. The only difference between seal member 934 and seal member 834 is that seal member 934 does not include openings that correspond to openings 851. The difference between outer protector member 964 and outer protector member 864 is that protector member 964 does not include stem portions 880 and that the collar portion 966 includes openings 978. The difference between inner protector member 962 and inner protector member 862 is that protector member 962 does not include openings 892 and that the collar portion 966 includes openings 978. The protector assembly 960 and seal member 934 are mounted in the trocar housing in a similar manner as discussed above with respect to the embodiment shown in FIGS. 2–6.

Figure 60:
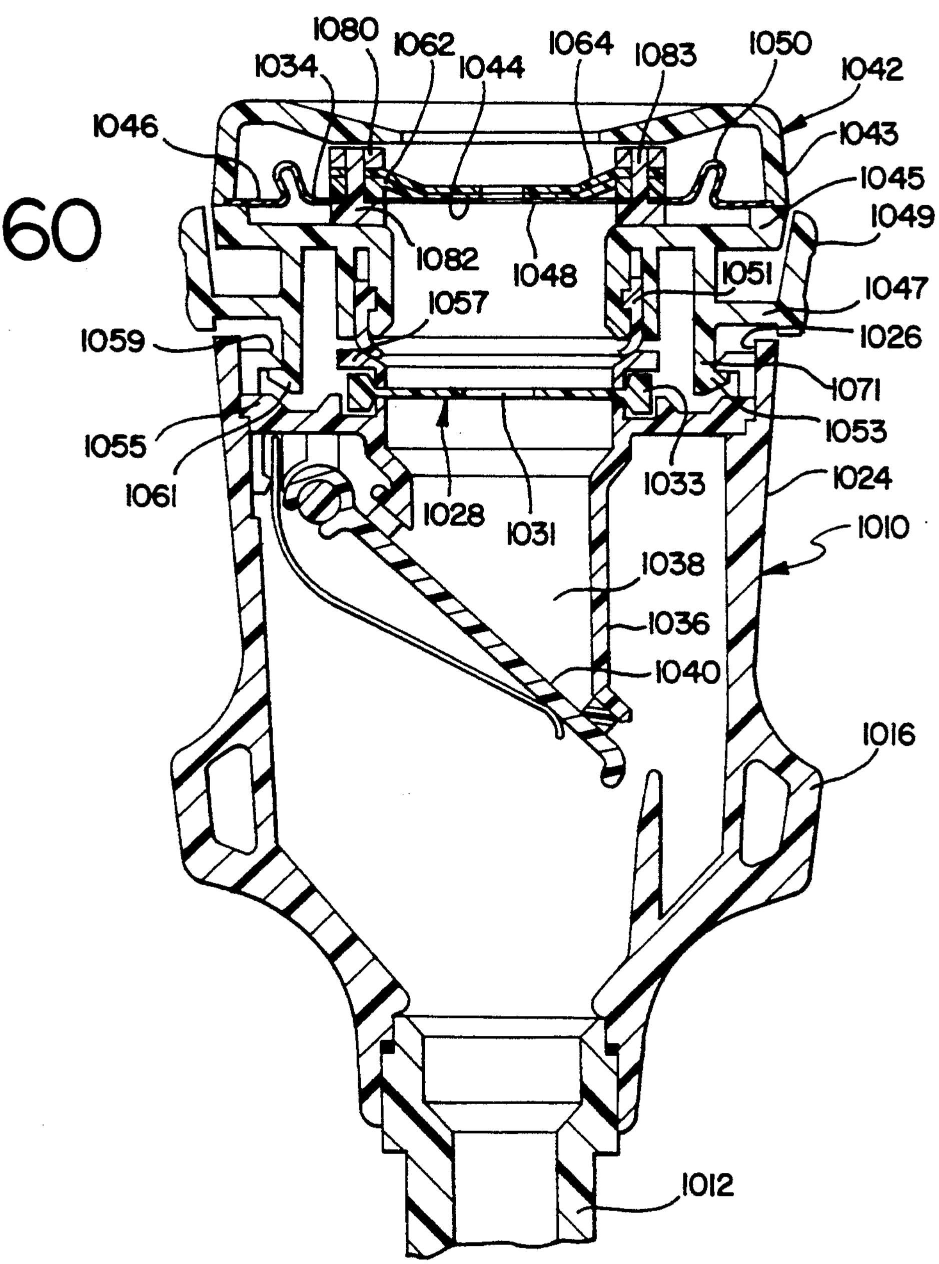
FIG. 60 is a cross-sectional view of a portion of a trocar assembly having an adaptor assembly that includes an alternative embodiment of a seal/protector assembly constructed in accordance with the invention wherein the seal/protector assembly is in a neutral orientation.
Figure 61:
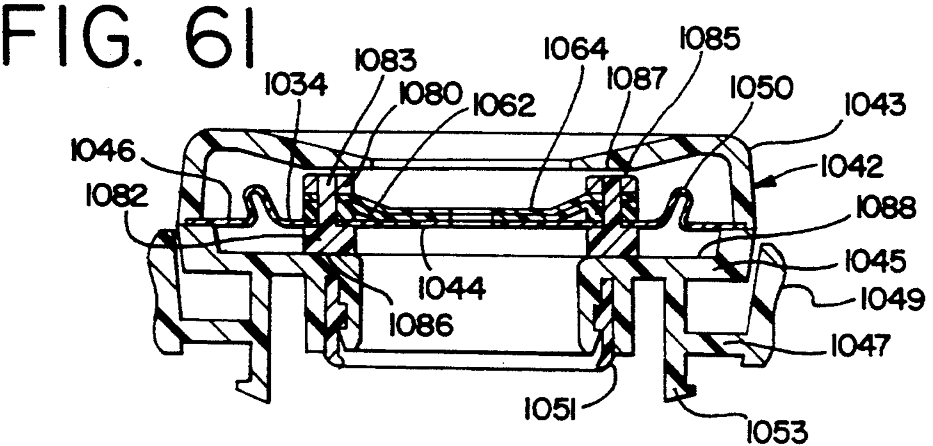
FIG. 61 is a cross-sectional view of the adaptor assembly that includes the seal/protector assembly as shown in FIG. 60.

FIG. 60 discloses a trocar assembly device 1010 that includes a trocar tube 1012, an obturator (not shown), and a housing or handle 1016. Handle 1016 has an open proximal end portion 1024 that defines an opening 1026. Opening 1026 is provided with a seal member assembly 1028 that includes a generally flat seal member 1033 having an opening 1031. Seal member 1033 cooperates with either an obturator, or the shaft of an elongated surgical instrument, extending through the housing to sealingly engage the outer surface thereof and thereby preclude the passage of fluids through handle 1016.

A flap valve assembly 1036 is suitably supported in end portion 1024. Flap valve assembly 1036 defines a passageway 1038 having a hinged flap valve 1040 at the distal end thereof and seal member 1033 at the proximal end thereof.

In accordance with the invention, an adaptor assembly 1042 is releasably attached to the proximal end portion 1024. Adaptor assembly 1042 is provided to increase the diameter range of instruments that may be extended through the trocar assembly and to enhance the sealing during an off-center entry of instruments therethrough. Adaptor assembly 1042 includes a housing portion 1043 and a latch portion 1045. Latch portion 1045 includes a latch member 1047 having a pair of outwardly extending flexible latch activator portions 1049 and latch finger portions 1071 defining a retaining flange portions 1053. A retaining portion 1055 associated with end portion 1024 defines a ramp section 1059 and a lip section 1061. As adaptor assembly 1042 is extended into end portion 1024, the finger portions 1071 of latch member 1045 contact a corresponding ramp section 1059 and are deflected inwardly as they ride down the ramp section. As the flange portions 1053 reach the lip sections they snap outwardly into locking engagement therewith. When it is necessary to remove the adaptor assembly, the activator portions 1049 are depressed inwardly causing the flange portions 1053 to move inwardly beyond the inner projections of lip sections 1061. An annular lip seal 1051 is suitably received by latch portion 1045 so as to seal against a cooperating surface 1057 associated with valve assembly 1036.

Adaptor assembly 1042 includes a seal member 1034 and a seal/protector assembly 1060 that includes an inner protector member 1062 and an outer protector member 1064. Seal member 1034 and protector members 1062 and 1064 are supported in housing portion 1043 in a unique manner that will be described below.

Figure 73:
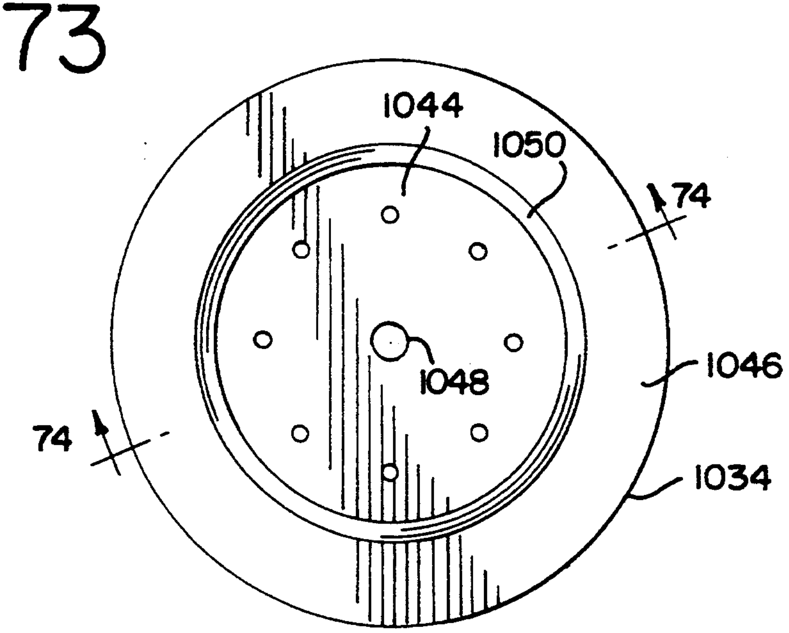
FIG. 73 is a top plan view of the seal member of the seal/protector assembly shown in FIG. 60.
Figure 74:
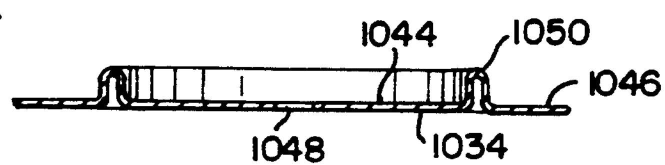
FIG. 74 is a cross-sectional view taken along line 74—74 in FIG. 73.

Referring to FIGS. 73–74, seal member 1034 includes a generally planar inner section 1044 and an outer section 1046. An opening 1048 is formed through inner section 1044 and is dimensioned to permit a medical instrument to pass therethrough in sealing engagement therewith. Opening 1048 is preferably smaller in diameter than opening 1031. A corrugated portion 1050 is formed in outer section 1046 in surrounding relationship with opening 1048. The peripheral edges of seal member 1034 are suitably attached to housing portion 1043.

Seal/protector assembly 1060 includes an inner protector member 1062 and an outer protector member 1064. Referring to FIGS. 69–70, outer protector member 1064 includes an annular collar portion 1066 and a pair of opposed leaf portions 1068 and 1070 formed integrally with collar portion 1066 so as to form a living hinge portion 1072 about which the leaf portions are able to pivot distally and proximally. The leaf portions 1068 and 1070 define an opening 1074 formed therethrough in axial alignment with the opening 1048 formed in seal member 1034. The collar portion 1066 is provided with circumferentially spaced apart openings 1078 formed therein.

Referring to FIGS. 71–72, outer protector member 1062 is of generally similar configuration as protector member 1064, with similar portions thereof identified with the same reference numeral. Outer protector member 1062 includes a collar portion 1066, a pair of leaf portions 1068 and 1070 that pivot about living hinge portions 1072, and an opening 1074. The collar portion 1066 is of increased thickness and is provided with openings 1078 that are formed therein.

Seal member 1034 and protector members 1062 and 1064 are attached together by an outer retainer ring 1080 and an inner retainer ring 1082. Referring to FIGS. 65–66, outer retainer ring 1080 is an annular member having openings 1081 formed therein that are in axial alignment with the openings 1078 formed in protector members 1062 and 1064. Referring to FIGS. 67–68, inner retainer ring 1082 is an annular member having posts 1083 projecting outwardly therefrom in axial alignment with the openings 1081 and 1078. Seal member 1034 and protector members 1062 and 1064 are sandwiched between rings 1080 and 1082 with posts 1083 extending through openings 1081 and 1078. The outer ends of posts 1083 are preferably suitably secured to ring 1080 by sonic welding or the like.

Seal/protector assembly 1060 is positioned within housing 1043 so as to permit lateral or transverse movement thereof. The respective outer surfaces 1085 and 1086 of the rings 1080 and 1082 cooperate with surfaces 1087 and 1088 of housing 1043 to retain and orient seal/protector assembly 1060.

Figure 62:
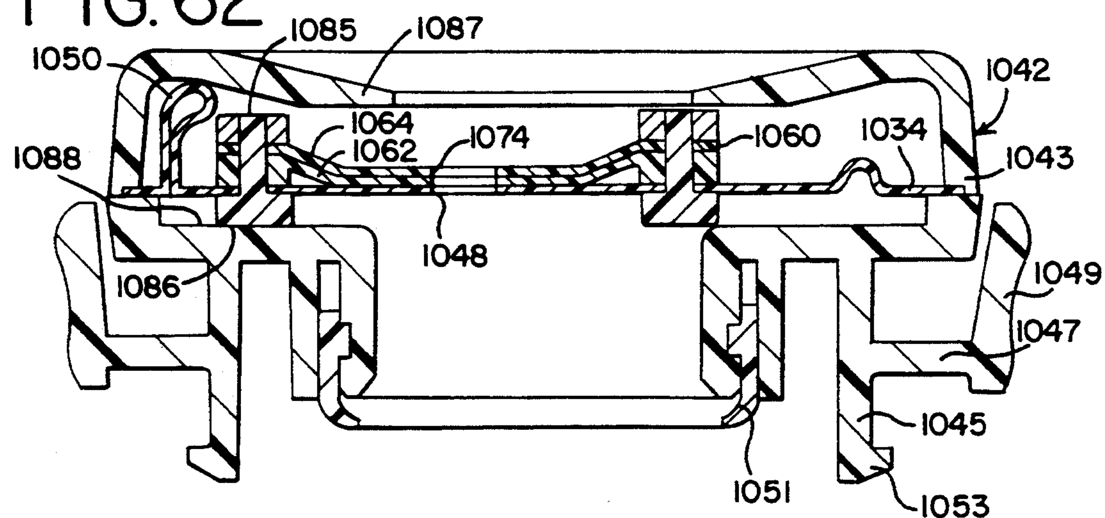
FIG. 62 is an enlarged cross-sectional view of the adaptor assembly shown in FIG. 61 wherein the seal/protector assembly is in a left off-center orientation.
Figure 63:
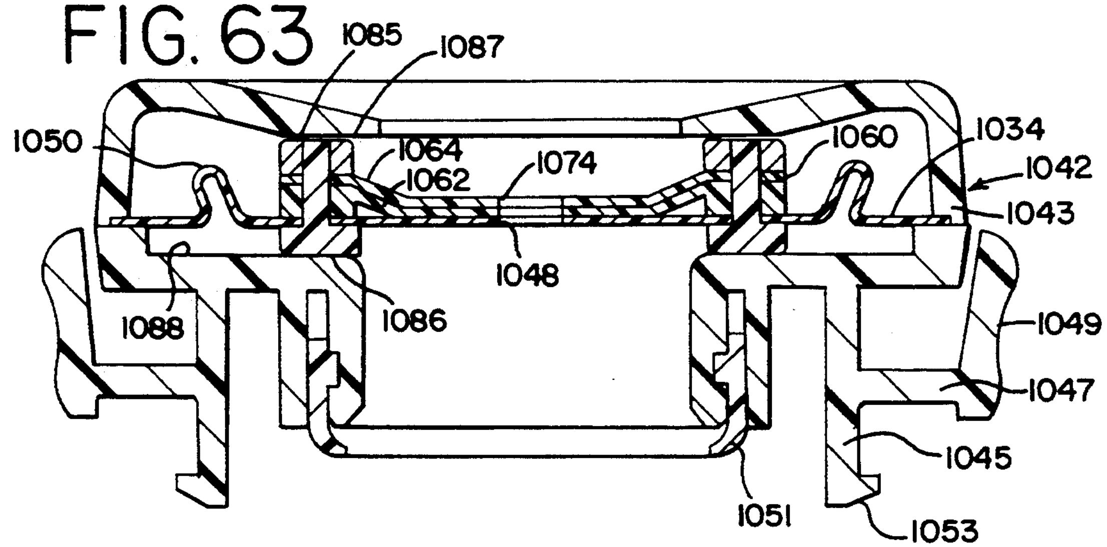
FIG. 63 is an enlarged cross-sectional view similar to FIG. 61.
Figure 64:
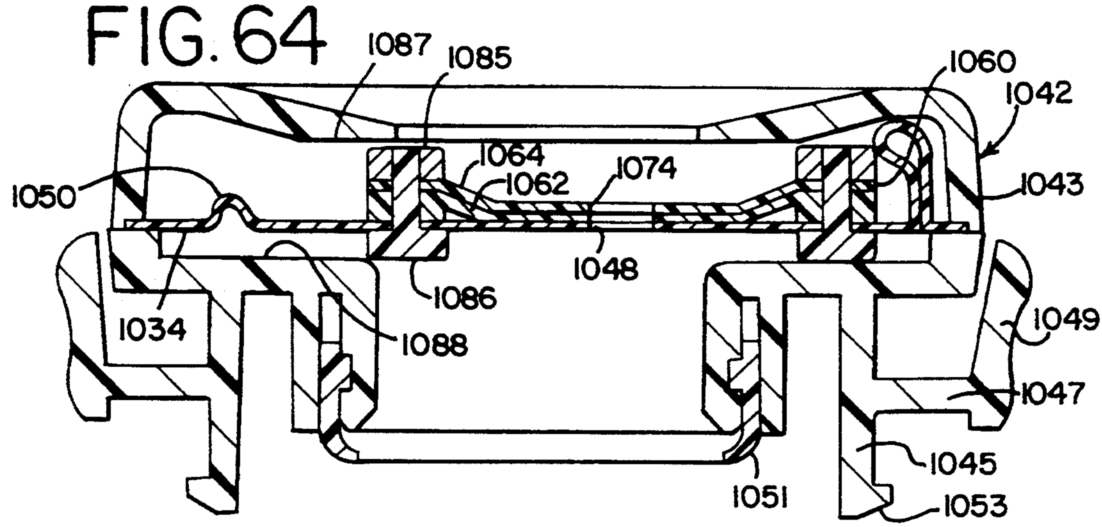
FIG. 64 is an enlarged cross-sectional view of the adaptor assembly shown in FIG. 61 wherein the seal/protector assembly is in a right off-center orientation.

In operation of the embodiment shown in FIGS. 60–74, an inserted elongate member contacts the leaf portions 1068 and cause them to pivot distally increasing the size of the open area 1074 in the outer protector 1064 and the inner protector member 1062 to permit the elongate member to pass therethrough. The distally moving leaf portions cause the opening 1048 in the seal member 1034 to dilate and increase in diameter. The inner edge of the seal member contacts and seals against the elongate member. Should the elongate member be positioned in an off-centered orientation, the seal/protector assembly 1060 is movable from the center orientation, as shown in FIG. 63, towards the left off-center orientation, as shown in FIG. 62, or the right off-center orientation, as shown in FIG. 64. Such movement maintains the seal in engagement with the elongate member extending through the seal/protector assembly.

Figure 75:
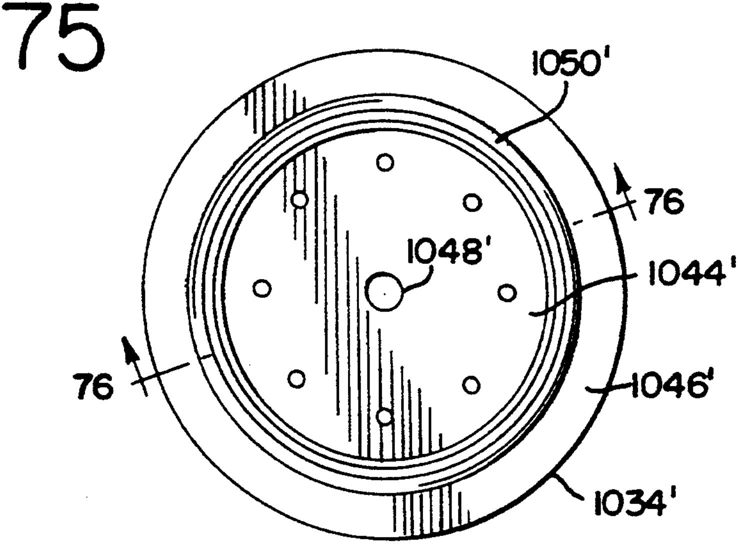
FIG. 75 is a top plan view of an alternative seal member for use in the seal/protector assembly shown in FIG. 60.
Figure 76:
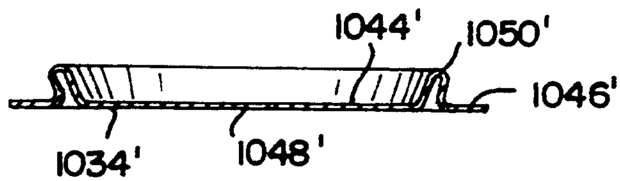
FIG. 76 is a cross-sectional view taken along line 76—76 in FIG. 75.

Referring to FIGS. 75 and 76, there is shown an alternative embodiment of the seal member as shown in FIGS. 73 and 74, wherein the corresponding elements of these seal member designs is identified with the same reference numerals followed by a prime sign. The corrugated portion 1050' is formed so as to extend outwardly towards the peripheral edge thereof, as best seen in FIG. 76.

Figure 77:
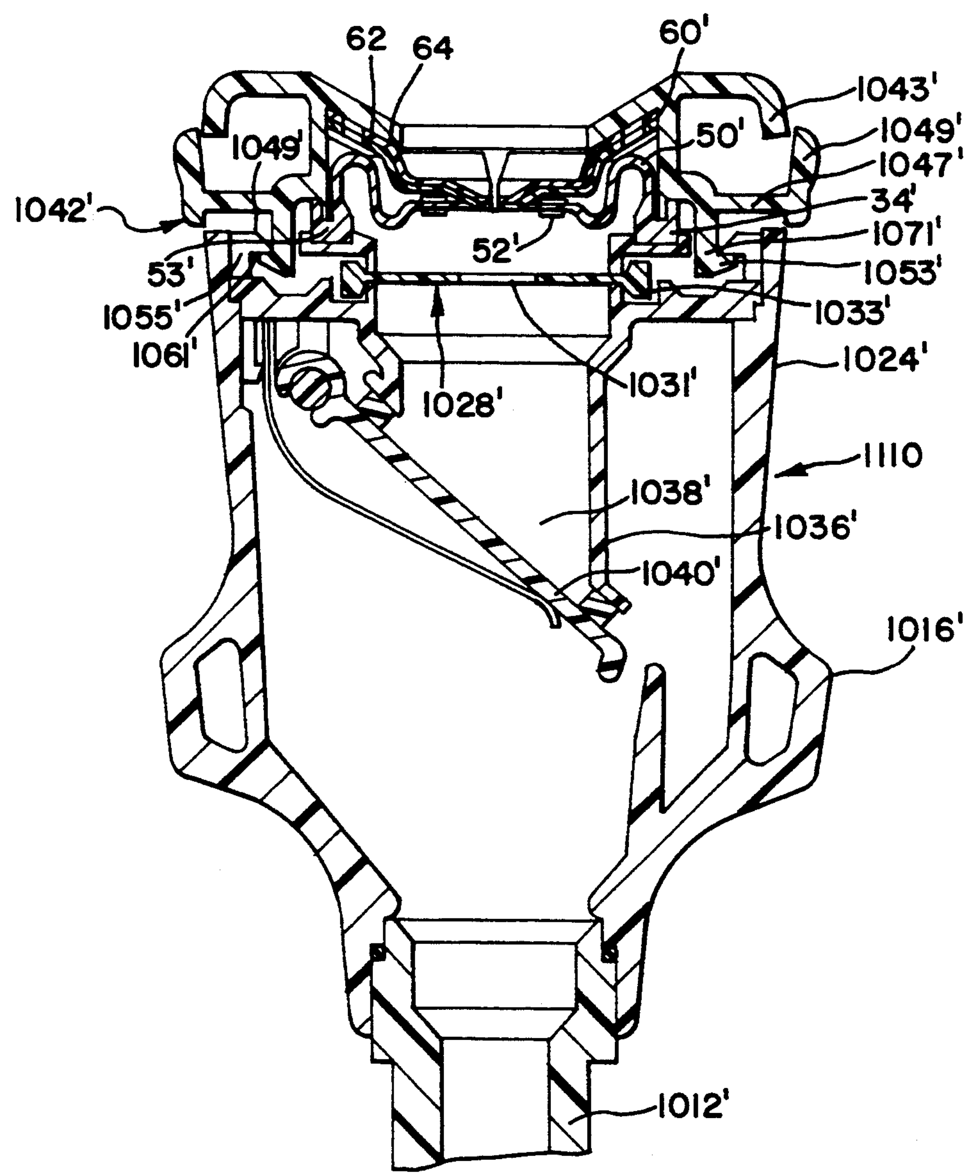
FIG. 77 is a cross-sectional view of a portion of a trocar assembly having an adaptor that includes a seal/protector assembly similar to that shown in FIG. 2.
Figure 78:
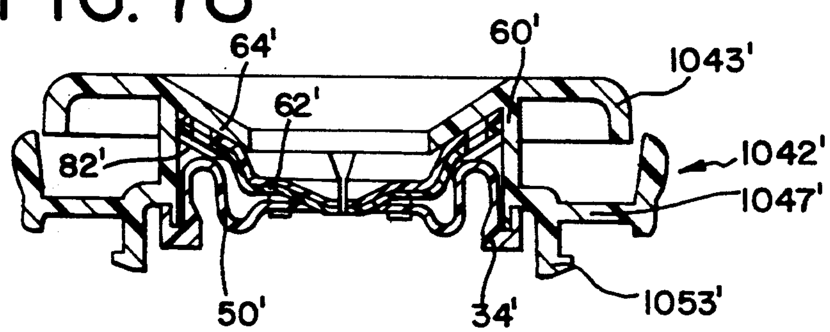
FIG. 78 is a cross-sectional view of the adaptor shown in FIG. 77.

Referring to FIGS. 77 and 78, there is shown an alternative trocar assembly device 1110 that in most respects is the same as the trocar assembly device 1010 discussed above except that it includes an alternative seal and seal/protector design. More specifically, the trocar assembly device 1110 includes a seal and seal/protector design similar to seal 34 and seal/protector 60 discussed above and shown in FIGS. 1–6. The elements in the trocar assembly device 1110 that correspond to elements in either the trocar assembly device 1010 or the seal 34 or seal/protector 60 are identified by the same reference numeral followed by a prime sign. In order to facilitate the disclosure of this embodiment, reference is made to the previous discussion of the structure and operation of these corresponding elements.

Figures 79, 80, 81:
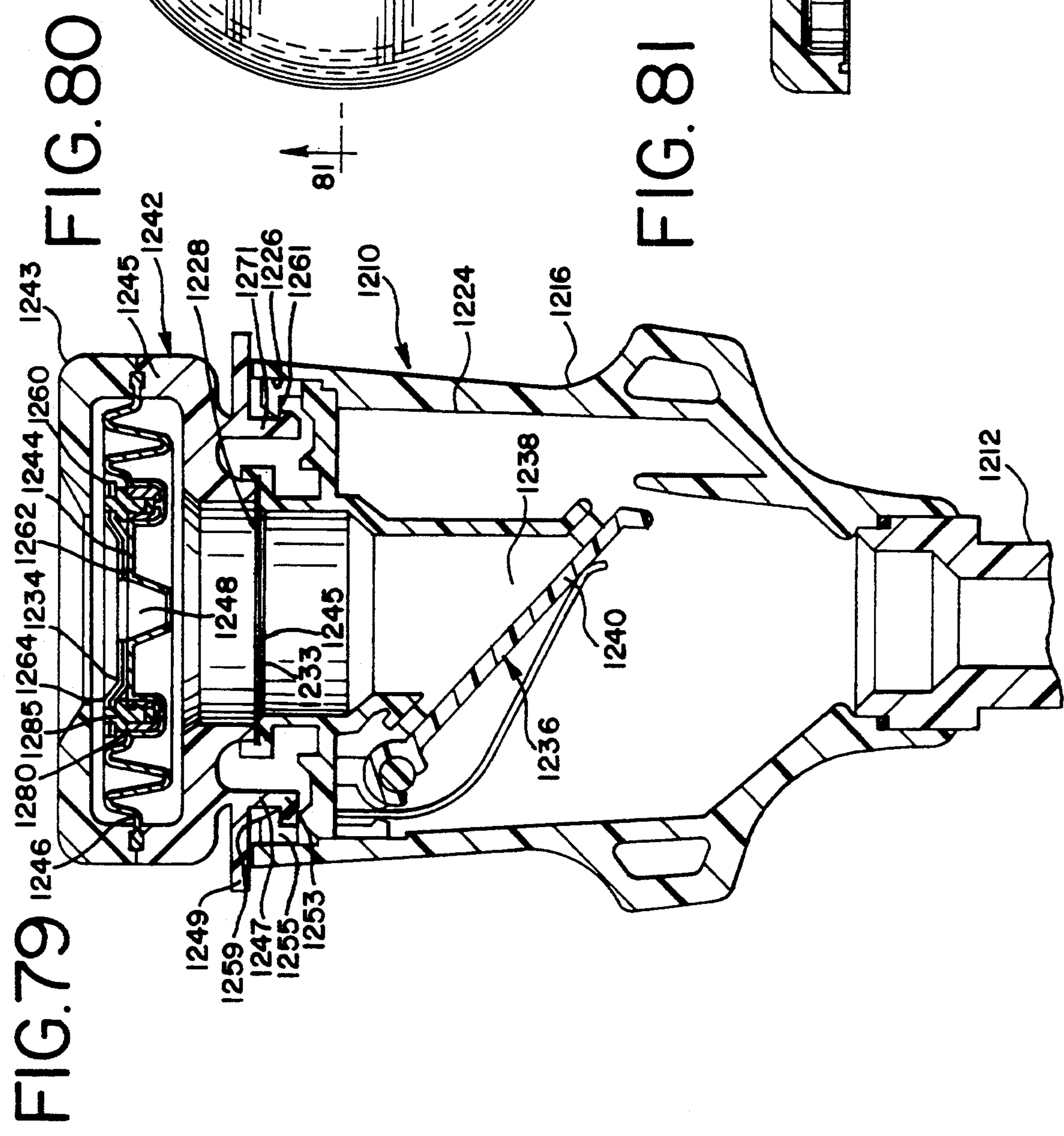
FIG. 79 is a cross-sectional view of a portion of a trocar assembly having an adaptor assembly that includes an alternative embodiment of a seal/protector assembly constructed in accordance with the invention.
FIG. 80 is a top plan view of an outer adaptor housing member of the adaptor assembly shown in FIG. 79.
FIG. 81 is a cross-sectional view taken along line 81—81 in FIG. 80.

A further alternative trocar assembly device 1210 in accordance with the invention is shown in FIG. 79. Trocar assembly device 1210 includes a trocar tube 1212, an obturator (not shown), and a housing or handle 1216. Handle 1216 has an open proximal end portion 1224 that defines an opening 1226. Opening 1226 is provided with a seal member assembly 1228 that includes a generally flat seal member 1233 having an opening 1245. Seal member 1233 cooperates with either an obturator, or an elongated surgical instrument, extending through the housing to sealingly engage the outer surface thereof and thereby preclude the passage of fluids through handle 1216.

A flap valve assembly 1236 is suitably supported in end portion 1224. Flap valve assembly 1236 defines a passageway 1238 having a hinged flap valve 1240 at the distal end thereof and seal member 1233 at the proximal end thereof.

Figure 88:
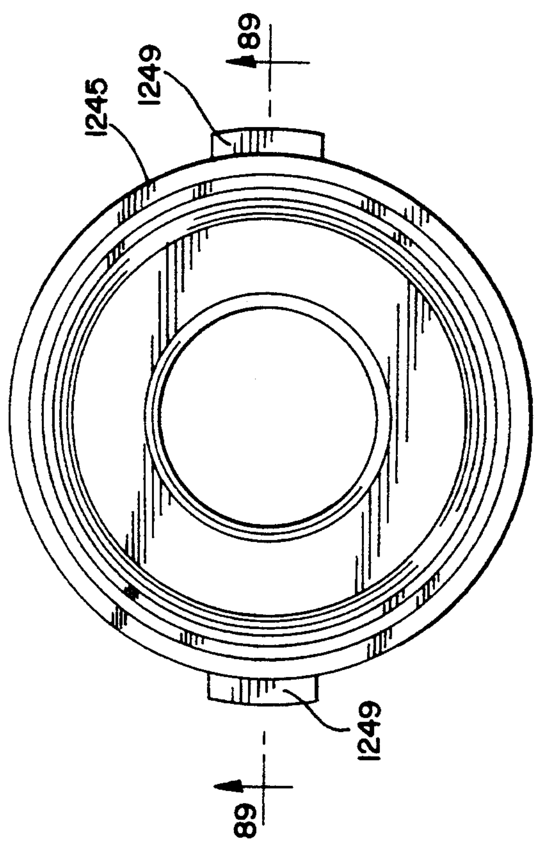
FIG. 88 is a top plan view of an inner adaptor housing member of the adaptor assembly shown in FIG. 87.
Figure 89:
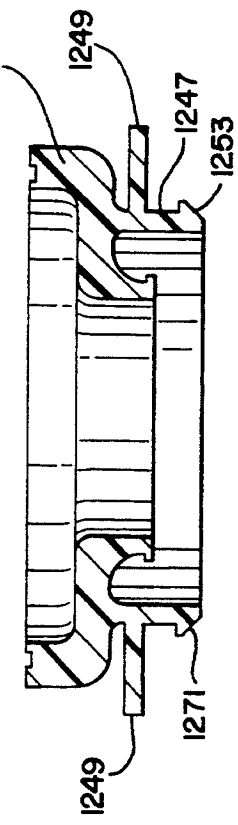
FIG. 89 is a cross-sectional view taken along line 89—89 in FIG. 88.

An adaptor assembly 1242 is releasably attached to the proximal end portion 1224. Adaptor assembly 1242 is provided to increase the diameter range of instruments that may be extended through the trocar assembly and to enhance the sealing during an off-center entry of instruments therethrough. Adaptor assembly 1242 includes an upper housing portion 1243, as shown in FIGS. 80–81, and a lower housing/latch portion 1245, as shown in FIGS. 88–89. Latch portion 1245 includes a latch member 1247 having a pair of outwardly extending flexible latch activator portions 1249 and latch finger portion 1271 defining retaining flange portions 1253. A retaining portion 1255 associated with end portion 1224 defines a ramp section 1259 and a lip section 1261. As adaptor assembly 1242 is extended into end portion 1224, the finger portions 1271 contact a corresponding ramp section 1259 and are deflected inwardly as they ride down the ramp section. As the flange portions 1253 reach the lip sections they snap outwardly into locking engagement therewith. When it is necessary to remove the adaptor assembly, the activator portions 1249 are depressed inwardly causing the flange portions 1253 to move inwardly beyond the inner projections of lip sections 1261.

Adaptor assembly 1242 includes a floating seal member 1234 and a seal/protector assembly 1260 that includes inner and outer protector members 1262 and 1264 respectively. Seal member 1264 and seal/protector assembly 1260 are uniquely configured and supported in housing portion 1243.

Figure 86:
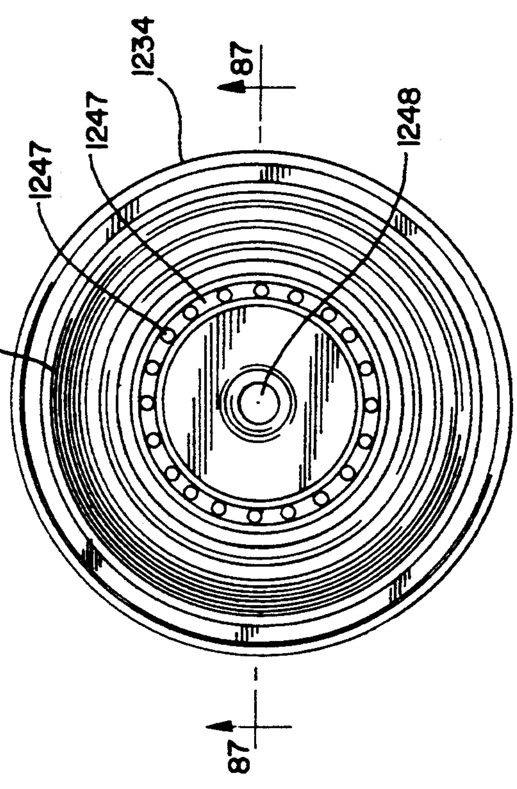
FIG. 86 is a top plan view of the seal member of the adaptor assembly shown in FIG. 79.
Figure 87:
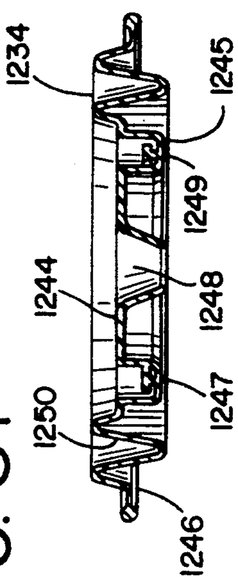
FIG. 87 is a cross-sectional view taken along line 87—87 in FIG. 86.

Referring to FIGS. 86–87, seal member 1234 includes an inner section 1244 and an outer section 1246. A funnel-shaped opening 1248 is formed through inner section 1244 and is dimensioned to permit a medical instrument to pass therethrough in sealing engagement therewith. Alternatively, opening 1248 may be flat. A corrugated portion 1250 is formed in outer section 1246 in surrounding relationship with opening 1248. The peripheral edges of seal member 1234 are suitably attached to housing portion 1243. An annular recess portion 1245 is formed between inner section 1244 and outer section 1246. A plurality of spaced apart, integrally formed connecting stem members 1247 extend upwardly from a base portion 1249 of recess portion 1245.

Figure 84:
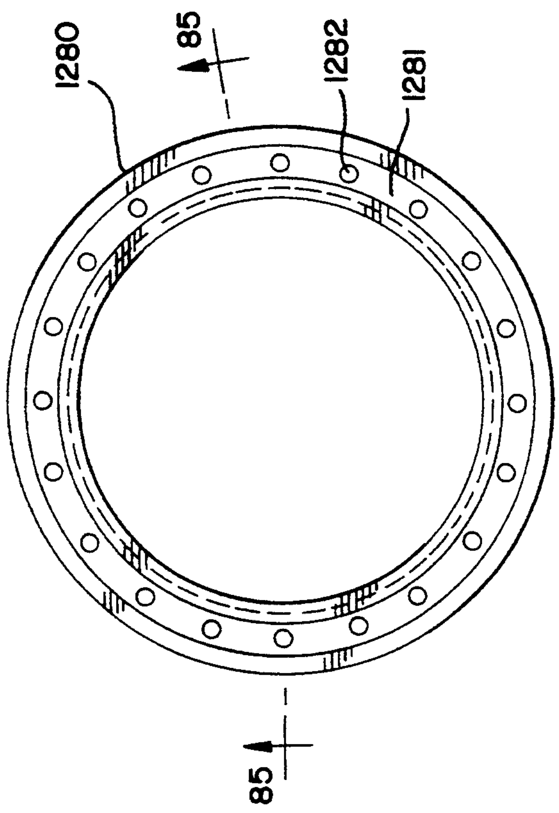
FIG. 84 is a top plan view of an insert member of the adaptor assembly shown in FIG. 79.
Figure 85:
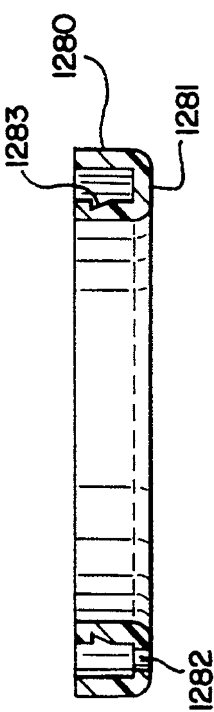
FIG. 85 is a cross-sectional view taken along line 85—85 in FIG. 84.
Figure 82:
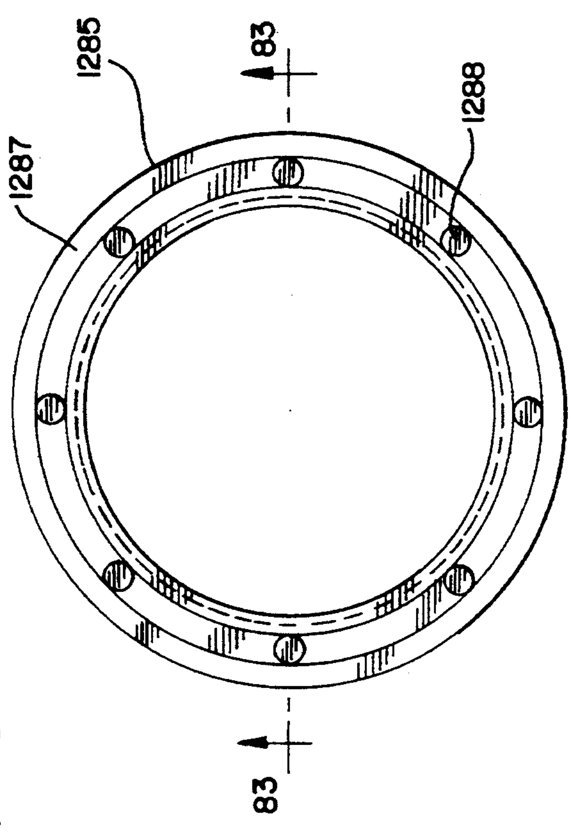
FIG. 82 is a top plan view of a protector holder member of the adaptor assembly shown in FIG. 79.
Figure 83:
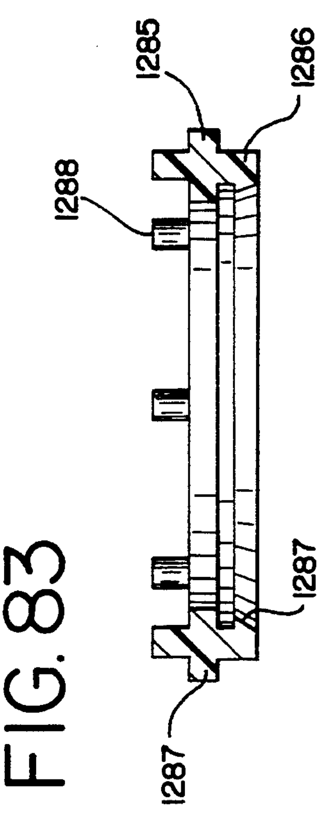
FIG. 83 is a cross-sectional view taken along line 83—83 in FIG. 82.

Referring to FIGS. 79, 84, and 85, a generally U-shaped seal insert 1280 is received within recess portion 1245. Insert 1280 has a base portion 1281 having a plurality of spaced apart openings 1282 through which the stem members 1247 extend to secure the insert 1280 to the seal member 1234. An annular notch 1283 is formed in the surface of the inner wall of the insert 1280. As shown in FIGS. 79, 82 and 83, a protector holder member 1285 is received within and attached to insert 1280. Holder 1285 includes an annular connecting portion 1286 that extends into insert 1280. Connecting portion 1286 is formed with a snap-in latch portion 1287 that is received in notch 1283 of insert 1280 as it is extended thereinto. A central portion 1287 of holder 1285 is positioned immediately adjacent the outer edges of insert 1280. A plurality of spaced apart protector mounting pins 1288 extend outwardly from central portion 1287.

Seal/protector assembly 1260 includes an inner protector member 1262 and an outer protector member 1264. The protector members 1262 and 1264 are configured similar to the protector member 1064 discussed above and shown in FIGS. 69 and 70. The pins 1288 extend through the openings formed in the collar portions of the protector members and are suitably secured thereto by sonic welding or the like. The seal 1234 and the seal/protector assembly 1260 are positioned within housing 1243 so as to permit floating lateral and longitudinal movement thereof.

The operation of the embodiment shown in FIGS. 79–89, is similar to that discussed above with respect to the embodiment shown in FIGS. 60–74 except that the seal/protector assembly has longitudinal movement in addition to lateral movement to further compensate for off-centered orientation of an elongate instrument extending therethrough.

Figure 90:
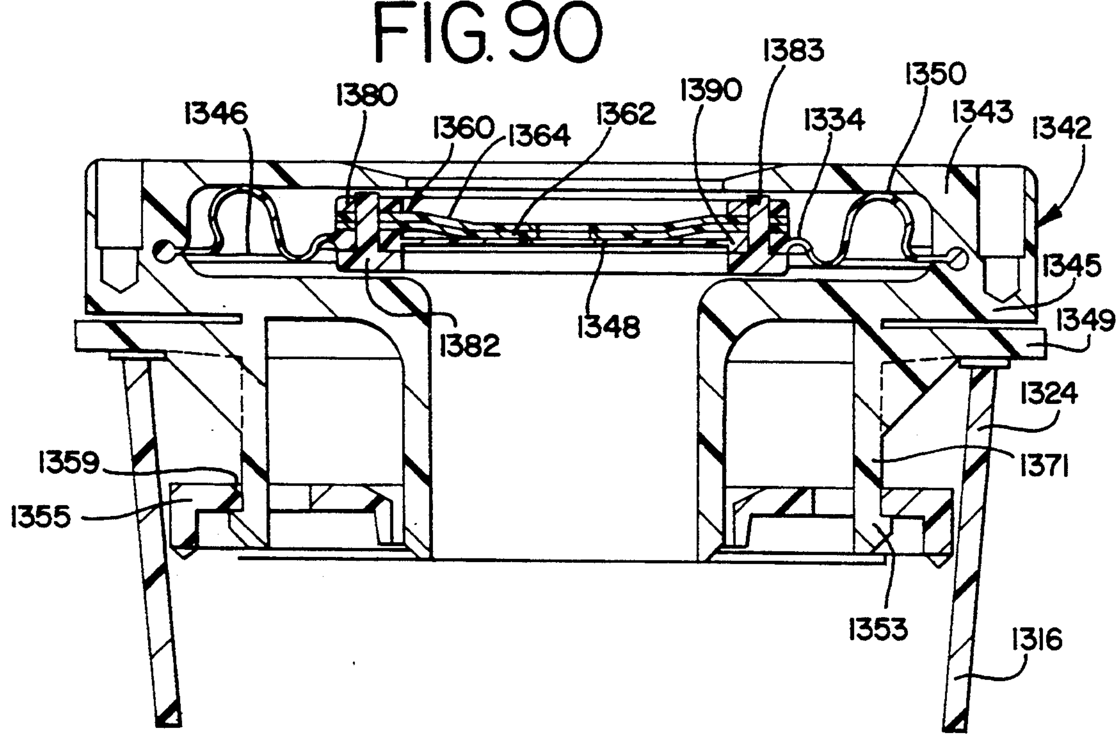
FIG. 90 is a cross-sectional view of a portion of a trocar assembly having an adaptor assembly that includes a further alternative embodiment of a seal/protector assembly constructed in accordance with the invention.
Figure 91:
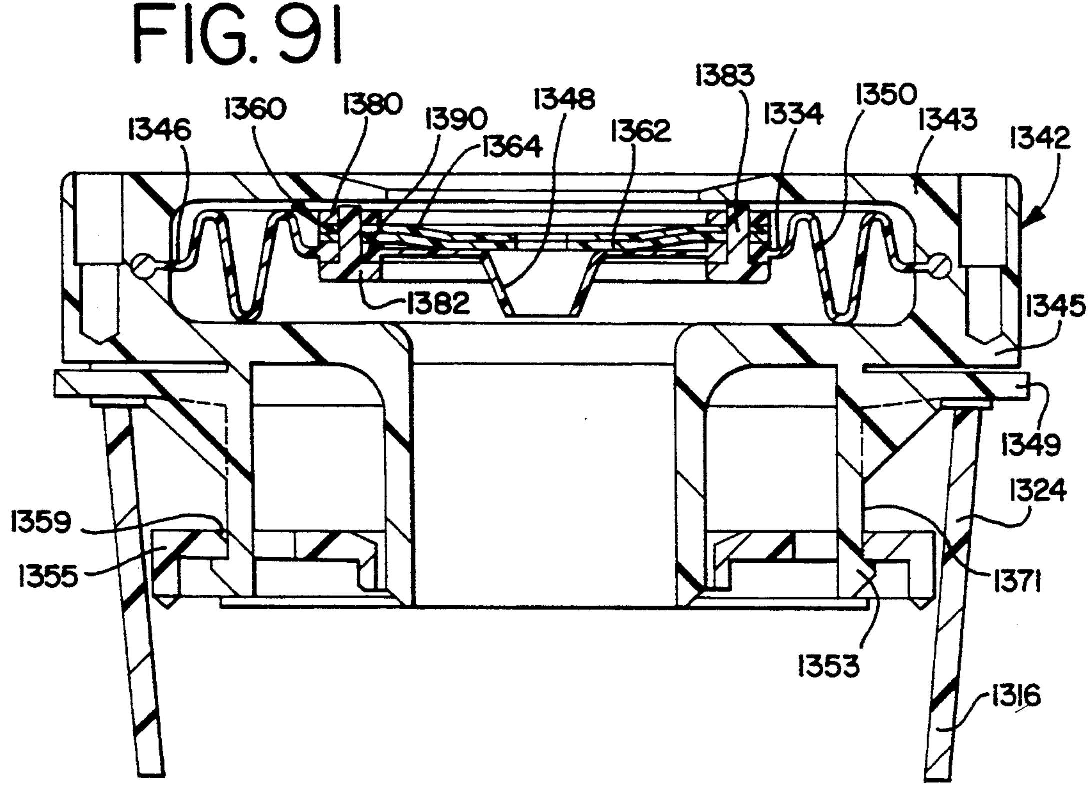
FIG. 91 is a cross-sectional view of the embodiment shown in FIG. 90 with a seal member having a funnel-shaped opening and the seal/protector assembly is mounted to permit lateral and axial movement thereof.

Referring to FIG. 90, there is shown yet another embodiment of a seal member 1334 and seal/protector assembly 1360 that is similar in design to the seal member 1034 and seal/protector assembly 1060 embodiment shown in FIGS. 60–74. The corresponding elements in these two embodiments are identified with reference numerals having the same last two digits. Reference is made to the above discussion of the seal member 1034 and the seal/protector assembly 1060 for a disclosure of the common features of the corresponding elements. The only significant difference between these two embodiments is the seal member 1334 is formed with an annular area 1390 of increased thickness adjacent to the corrugated portion 1350 and the inner protector member 1362 is of the same construction as the outer protector member 1364. The embodiment shown in FIG. 91 is of the same construction as the embodiment shown in FIG. 90 except that the seal member is provided with a funnel-shaped opening 1348 and the seal/protector assembly floats within the housing in a similar manner as discussed above with respect to seal/protector assembly 1260.

From the foregoing it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modification as fall within the scope of the claims.

What is claimed is:

1. A trocar assembly for providing communication into an anatomical cavity, comprising:

(a) a trocar tube defining an interior lumen having an open distal end portion and an open proximal end portion and further defining a long axis for accommodating axial movement of an elongate instrument of lesser cross-sectional dimension therethrough;

(b) a housing adjoining said proximal end portion of said trocar tube defining a chamber having open distal end portion and a proximal end portion that communicate with said lumen and permit axial movement of an elongate instrument therethrough;

(c) an elastomeric seal member positioned in said chamber for sealing said proximal end portion of said chamber, said seal member having an opening formed therein for permitting an elongate instrument to pass therethrough in sealing engagement therewith; and (d) a seal/protector assembly positioned in said chamber adjacent to and proximally of said seal member in a facing relationship thereto for protecting said seal member as an elongate instrument moves axially through said seal member, said seal/protector assembly including at least two protector members positioned adjacent to and in alignment with one another along said long axis, each of said protector members having an integrally formed annular collar portion and at least one leaf portion formed integrally with said collar portion defining a living hinge portion at the intersection thereof about which said leaf portion is able to pivot distally and proximally, said leaf portions defining an opening therethrough in axial alignment with the opening in said seal member such that axial movement of an elongate instrument into contact with said leaf portions causes said leaf portions to pivot distally and thereby increase the size of the opening formed in said protector members to permit an elongate instrument to pass therethrough and then through the opening in said seal member without causing damage to said seal member.

2. The invention as defined in claim 1 wherein a leaf portion of each protector member is oriented with respect to a leaf portion of an immediately adjacent protector member so that such leaf portions are not in axial alignment with one another.

3. The invention as defined in claim 2 wherein said protector assembly includes an inner protector member and an outer protector member, said inner and outer protector members each including a pair of opposed leaf portions that occupy a substantial portion of the area defined within said collar portion.

4. The invention as defined in claim 2 wherein the collar portion of each of said protector members is secured to said housing.

5. The invention as defined in claim 4 wherein said collar portions have a plurality of spaced apart openings formed therein and said housing includes mounting pins that extend through a corresponding opening in said collar portions.

6. The invention as defined in claim 5 wherein said openings in said collar portions are elongated in a radial direction so as to permit limited lateral movement of said protector members within said housing.

7. The invention as defined in claim 6 wherein an annular spacer ring is positioned between said inner protector member and said seal member.

8. The invention as defined in claim 3 wherein each of said leaf portions is generally concave and defines an inner edge portion that is parallel and immediately adjacent the inner edge portion of the other leaf portion.

9. The invention as defined in claim 2 wherein said protector assembly includes an inner protector member, an outer protector member and an intermediate protector member positioned between said inner protector member and said outer protector member.

10. The invention as defined in claim 9 wherein each of said protector members includes a single leaf member that occupies a substantial portion of the area defined within said collar portion.

11. The invention as defined in claim 10 wherein said leaf portions associated with each of said protector members is oriented with respect to one another so as to close the area defined within said collar portions except for said opening in axial alignment with the opening in said seal member.

12. The invention as defined in claim 11 wherein each of said leaf members occupies about two-thirds of the area defined within each of said collar portions.

13. The invention as defined in claim 2 wherein said protector assembly includes an inner protector member and an outer protector member, said inner and outer protector members each including four generally pie-shaped leaf portions that occupy a substantial portion of the area defined within said collar portion.

14. The invention as defined in claim 13 wherein the collar portion of each of said protector members is secured to said housing.

15. The invention as defined in claim 14 wherein said collar portions have a plurality of spaced apart openings formed therein and said housing includes mounting pins that extend through a corresponding opening in said collar portions.

16. The invention as defined in claim 1 wherein said seal member has an outer surface that has an annular recess portion formed therein and the protector member adjacent said seal member has an annular section that is received in said recess portion.

17. The invention as defined in claim 16 wherein said recess portion is defined by an annular ramp portion extending outwardly from the outer surface of said seal member.

18. A trocar assembly for providing communication into an anatomical cavity, comprising:

(a) a trocar tube defining an interior lumen having an open distal end portion and an open proximal end portion for accommodating axial movement of an elongate instrument of lesser cross-sectional dimension therethrough;

(b) a housing adjoining said proximal end portion of said trocar tube defining a chamber having open distal end portion and a proximal end portion that communicate with said lumen and permit axial movement of an elongate instrument therethrough;

(c) an elastomeric seal member positioned in said chamber for sealing said proximal end portion of said chamber, said seal member having an opening formed therein for permitting an elongate instrument to pass therethrough in sealing engagement therewith; and (d) a seal/protector assembly positioned in said chamber adjacent to and proximally of said seal member in a facing relationship thereto for protecting said seal member as an elongate instrument moves axially through said seal member, said seal/protector assembly including an inner protector member and an outer protector member positioned adjacent to and in axial alignment with one another, said inner and outer protector members having an integrally formed annular collar portion and at least one leaf portion formed integrally with said collar portion defining a living hinge portion at the intersection thereof about which said leaf portions are able to pivot distally and proximally, said leaf portions of said inner protector member being oriented with respect of said leaf portions of said outer protector member so that said leaf portions are not in axial alignment with one another, said leaf portions defining an opening therethrough in axial alignment with the opening in said seal member such that axial movement of an elongate instrument into contact with said leaf portions causes said leaf portions to pivot distally increasing the size of the opening formed in said protector members to permit an elongate instrument to pass therethrough and then through the opening in said seal member without causing damage to said seal member.

19. The invention as defined in claim 18 wherein at least one of said protector members is attached to said seal member.

20. The invention as defined in claim 19 wherein said outer protector member having a plurality of spaced apart distally extending stem portions, said inner protector member having openings through which said stem portions extend, and said seal member having openings through which said stem portions extend.

21. The invention as defined in claim 20 wherein said stems are formed so as to maintain said inner protector member in contact with said seal member.

22. The invention as defined in claim 21 wherein said seal member is formed with a corrugated portion and said openings in said seal member extend through said corrugated portion.

23. The invention as defined in claim 19 wherein said seal member is formed with an inwardly extending annular flange that defines an inwardly opening cavity adjacent said opening in said seal member and said outer protector member is formed with a flange portion that is received within said cavity.

24. The invention as defined in claim 18 wherein said seal member is funnel-shaped and said inner and outer protector members have at least one funnel-shaped leaf portion.

25. The invention as defined in claim 18 wherein said seal member includes a plurality of spaced apart ribs that extend outwardly from an outer surface thereof and said inner protector member includes a plurality of spaced apart recess portions for receipt of a corresponding rib therein.

26. The invention as defined in claim 25 wherein said ribs and said recess portions extend radially with respect to said opening in said seal member.

27. The invention as defined in claim 26 wherein said outer protector member is provided with an annular rib portion extending from the inner surface thereof to create a space between said outer protector member and said inner protector member adjacent said opening in said seal member.

28. The invention as defined in claim 18 wherein said seal member includes an inner section and an outer section, said outer section having a peripheral edge that is attached to said housing.

29. The invention as defined in claim 28 wherein a corrugated portion is formed in said outer portion of said seal member.

30. The invention as defined in claim 29 wherein said collar portions of said protector members are attached to said inner section of said seal member so as to permit lateral movement thereof within said housing to accommodate off-center orientation of an elongate instrument extending therethrough.

31. The invention as defined in claim 30 wherein said collar portions of said protector members and said seal member have spaced apart axially aligned opening formed therein.

32. The invention as defined in claim 31 wherein said protector members are attached to said seal member by an annular inner retainer ring that has posts projecting outwardly therefrom extending through corresponding openings in said protector members and said seal member and an annular outer retainer ring having openings formed therein to receive the outer ends of said posts.

33. The invention as defined in claim 32 wherein said housing includes spaced apart parallel surfaces that cooperate with outer surfaces of said inner retainer ring and said outer retainer ring to limit axial movement of said protector members.

34. The invention as defined in claim 30 wherein an annular recess is formed between said inner section and said outer section of said seal member having a plurality of spaced apart stem members extending upwardly from a base portion thereof.

35. The invention as defined in claim 34 wherein a generally U-shaped seal insert is received within said recess, said insert including a base portion having a plurality of spaced apart openings through which said stem members extend to secure said insert to said seal member.

36. The invention as defined in claim 35 wherein a protector holder member is received within said insert, said protector holder member having a plurality of spaced apart protector mounting pins that extend through corresponding openings formed in said collar portions of said protector members.

37. The invention as defined in claim 36 wherein said insert has a wall portion that has an annular notch formed therein and the protector holder member has a snap-in latch portion that is received in said notch to secure said protector holder to said insert.

38. The invention as defined in claim 36 wherein said protector members and said inner section of said seal member float within said housing permitting lateral and axial movement thereof as an elongate member extends therethrough in off-centered orientation.

39. The invention as defined in claim 18 wherein said seal member has a distally projecting funnel-shaped portion defining said opening.

40. A seal/protector assembly for use in protecting an elastomeric seal member in a trocar assembly as an elongate instrument moves axially through the seal member, said seal/protector assembly comprising:

at least two protector members positioned adjacent to and in axial alignment with one another;

each of said protector members having an integrally formed annular collar portion and at least one leaf portion formed integrally with said collar portion defining living hinge portion at the intersection thereof about which said leaf portion is able to pivot; and said leaf portions defining an opening therethrough.

41. The invention as defined in claim 40 wherein a leaf portion of each protector member is oriented with respect to a leaf portion of an immediately adjacent protector member so that such leaf portions are not in axial alignment with one another.

42. The invention as defined in claim 41 wherein said protector assembly includes an inner protector member and an outer protector member, said inner and outer protector members each including a pair of opposed leaf portions that occupy a substantial portion of the area defined within said collar portion.

43. The invention as defined in claim 42 wherein each of said leaf portions is generally concave and defines an inner edge portion that is parallel and immediately adjacent the inner edge portion of the other leaf portion.

44. The invention as defined in claim 41 wherein said protector assembly includes an inner protector member, an outer protector member and an intermediate protector member positioned between said inner protector member and said outer protector member.

45. The invention as defined in claim 44 wherein each of said protector members includes a single leaf member that occupies a substantial portion of the area defined within said collar portion.

46. The invention as defined in claim 45 wherein said leaf portions associated with each of said protector members is oriented with respect to one another so as to close the area defined within said collar portions except for said opening in axial alignment with the opening in said seal member.

47. The invention as defined in claim 46 wherein each of said leaf members occupies about two-thirds of the area defined within each of said collar portions.

48. The invention as defined in claim 41 wherein said protector assembly includes an inner protector member and an outer protector member, said inner and outer protector members each including four generally pie-shaped leaf portions that occupy a substantial portion of the area defined within said collar portion.

* * * * *